US012691092B2

(12) United States Patent
Bayat

(10) Patent No.: US 12,691,092 B2
(45) Date of Patent: Jul. 28, 2026

(54) METHOD FOR REDUCING CUTANEOUS SKIN SCARRING BY PRE-EMPTIVE PRIMING AND COMPOUNDS AND COMPOSITIONS FOR ITS IMPLEMENTATION

(71) Applicant: SOS SCIENCE OF SKIN LTD, Worcestershire (GB)

(72) Inventor: Ardeshir Bayat, Worcestershire (GB)

(73) Assignee: SOS SCIENCE OF SKIN LTD, Worcestershire (GB)

( * ) Notice: Subject to any disclaimer, the term of this patent is extended or adjusted under 35 U.S.C. 154(b) by 494 days.

(21) Appl. No.: 18/043,367

(22) PCT Filed: Aug. 25, 2021

(86) PCT No.: PCT/GB2021/052209

§ 371 (c)(1),
(2) Date: Feb. 28, 2023

(87) PCT Pub. No.: WO2022/043687

PCT Pub. Date: Mar. 3, 2022

(65) Prior Publication Data

US 2024/0016776 A1 Jan. 18, 2024

(30) Foreign Application Priority Data

Aug. 28, 2020 (GB) ..................................... 2013586

(51) Int. Cl.
*A61K 31/352* (2006.01)
*A61K 9/00* (2006.01)
*A61P 17/02* (2006.01)

(52) U.S. Cl.
CPC .......... *A61K 31/352* (2013.01); *A61K 9/0014* (2013.01); *A61P 17/02* (2018.01)

(58) Field of Classification Search
CPC ...... A61K 31/353; A61K 9/0014; A61P 17/02
See application file for complete search history.

(56) References Cited

U.S. PATENT DOCUMENTS

2008/0038381 A1 2/2008 Le et al.
2009/0234382 A1 * 9/2009 Dillon .................... A61Q 19/02 606/204.35

FOREIGN PATENT DOCUMENTS

CN 111544759 A 8/2020

OTHER PUBLICATIONS

Kapoor et al (The American Journal of Pathology, 2004, vol. 165, pp. 299-307) (Year: 2004).*
Ud-Din et al (Journal of Investigative Dermatology, Aug. 2019, vol. 139, pp. 1680-1690) (Year: 2019).*
International Search Report and Written Opinion dated Dec. 9, 2021, pertaining to Int'l Patent Application No. PCT/GB2021/052209, 11 pgs.
Ud-Din et al. "A Double-Blind, Randomized Trial Shows the Role of Zonal Priming and Direct Topical Application of Epigallocatechine-3-Gallate in the Modulation of Cataneous Scarring in Human Skin", Journal of Investigative Dermatology (2019) vol. 139, pp. 1680-1690.

* cited by examiner

*Primary Examiner* — Mark V Stevens
(74) *Attorney, Agent, or Firm* — DINSMORE & SHOHL LLP

(57) ABSTRACT

A method of enhancing the quality of a skin scar by topical application of an agent for improving scar quality is characterised in that said agent is pre-emptively applied to a potential surgical cutaneous site in advance of surgery, including surgery involving use of lasers. The topical agent may be a polyphenol, such as (-)-epigallocatechin-3-gallate (EGCG). Use of such a topical agent in advance of surgery leads to significant beneficial effects on dermal scarring by reducing mast cells, angiogenesis, skin thickness and simultaneously increasing elastin content. The topical agent may be applied directly or incorporated in a dressing, such as in a dermal patch comprising an adhesive silicone sheet, and can be worn both in the lead up to surgery and post-operatively.

15 Claims, 36 Drawing Sheets

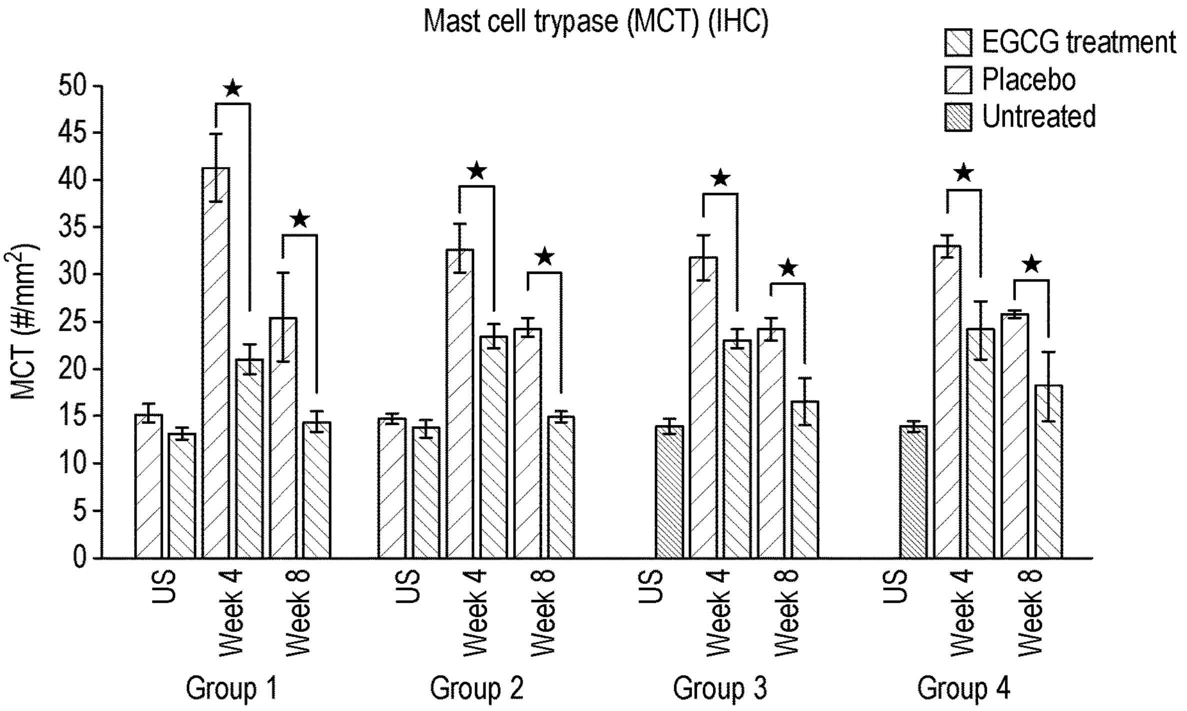
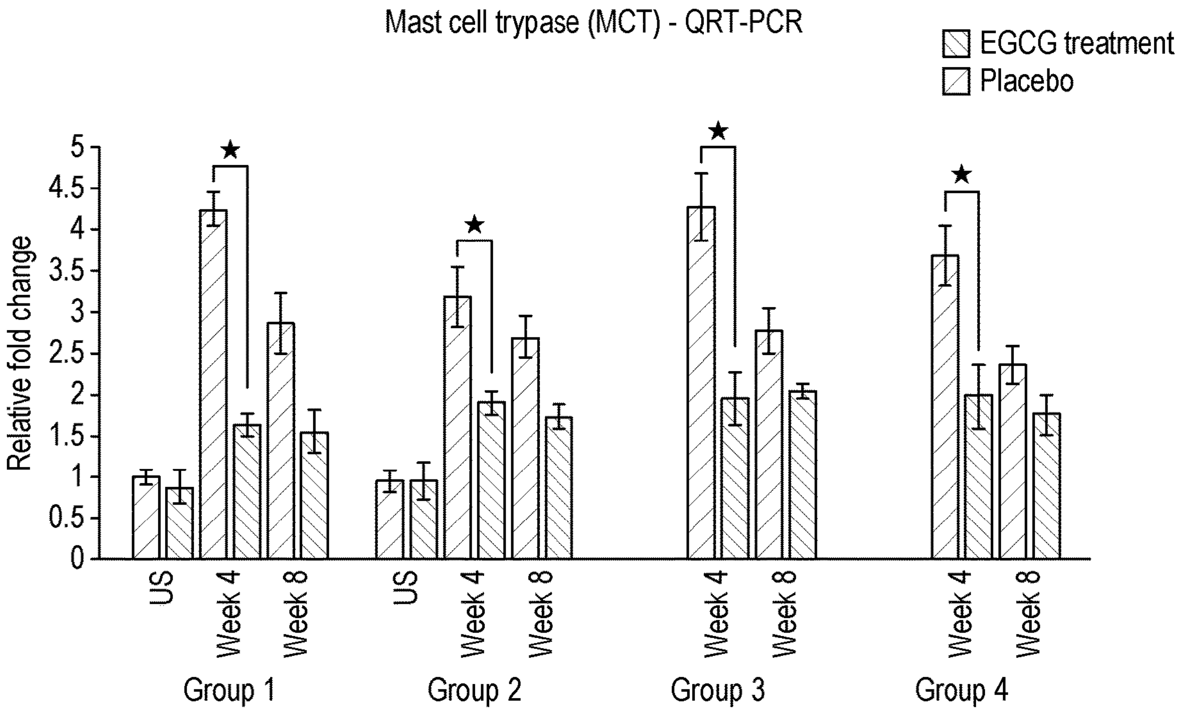
FIG. 3a Cont'd

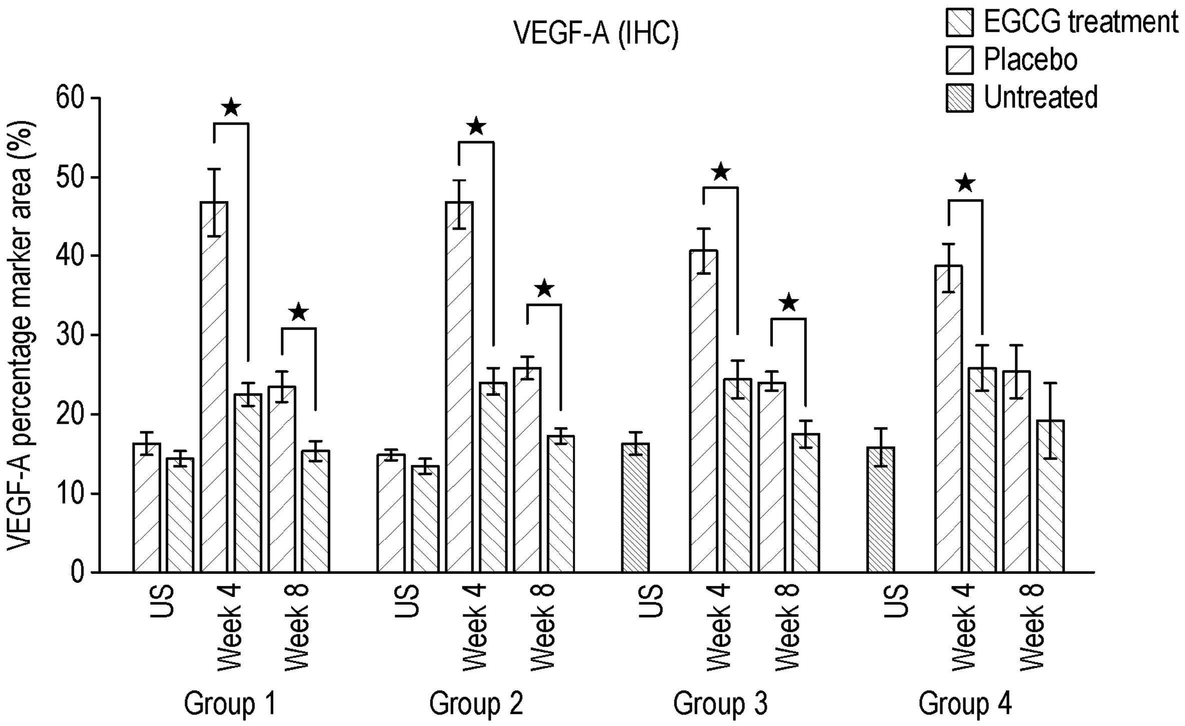
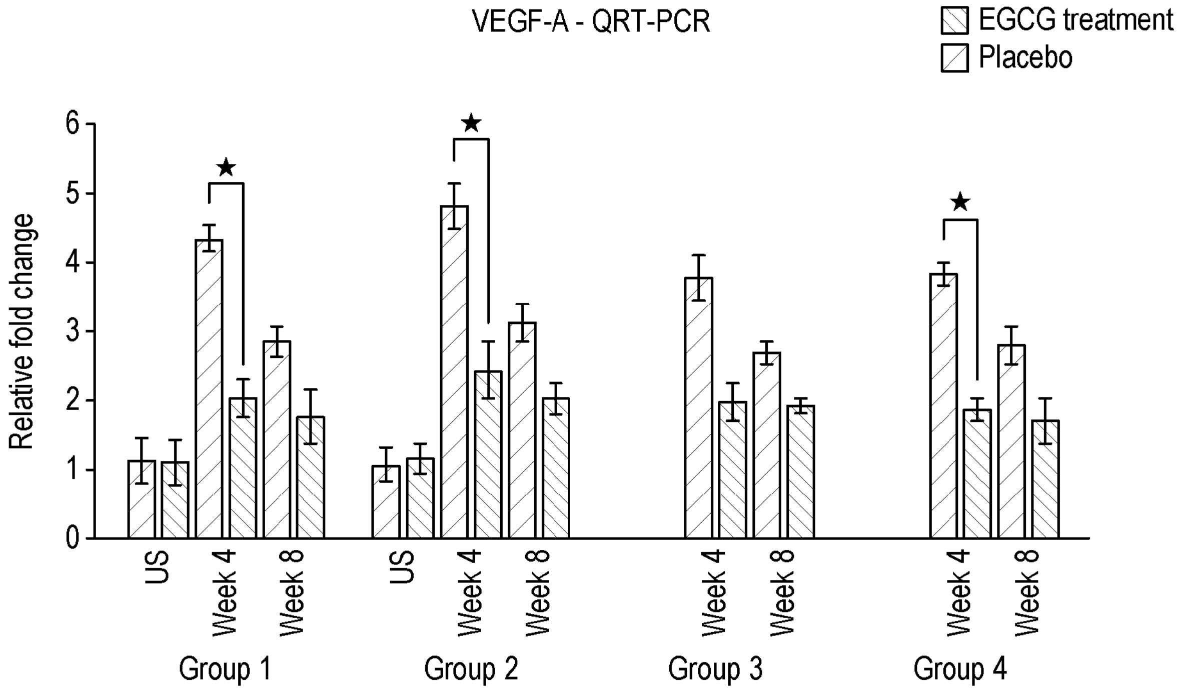
FIG. 7b Cont'd

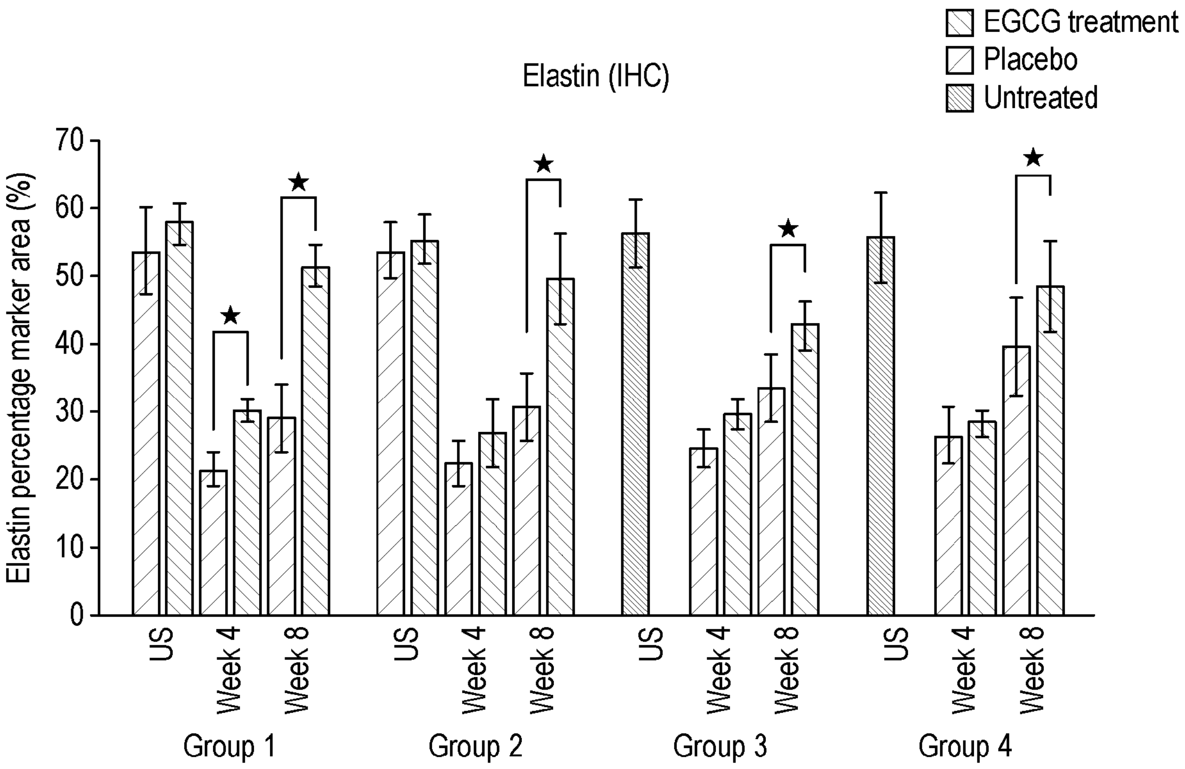
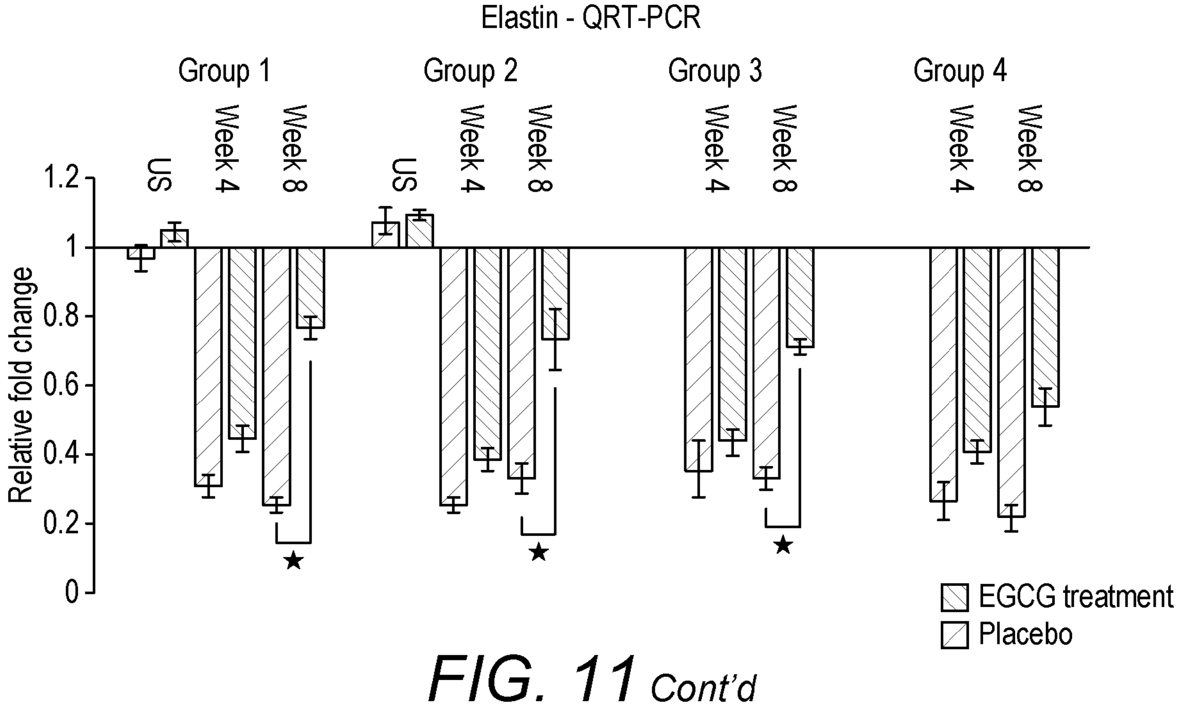
FIG. 11 Cont'd

Percentage differences between placebo and EGCG arms

| Parameter | Marker | Group 1 | | | Group 2 | | | Group 3 | | | Group 4 | | |
|---|---|---|---|---|---|---|---|---|---|---|---|---|---|
| | | Day 0 | Week 4 | Week 8 | Day 0 | Week 4 | Week 8 | Day 0 | Week 4 | Week 8 | Day 0 | Week 4 | Week 8 |
| Mast cells | MCT | -17 | -108 | -56 | -7 | -50 | -57 | N/A | -55 | -49 | N/A | -56 | -49 |
| | MCC | -16 | -80 | -23 | -15 | -68 | -19 | N/A | -51 | -26 | N/A | -39 | -21 |
| | CKIT | -18 | -78 | -55 | -16 | -53 | -45 | N/A | -52 | -50 | N/A | -51 | -43 |
| Angiogenesis | FLPI (clinical blood flow) | -5 | -10 | -27 | -8 | -31 | -31 | N/A | -18 | -29 | N/A | -67 | -42 |
| | D-OCT (clinical) blood flow | -22 | -57 | -61 | -24 | -34 | -77 | N/A | -45 | -28 | N/A | -42 | -24 |
| | CD31 | -11 | -103 | -57 | -10 | -77 | -53 | N/A | -77 | -47 | N/A | -63 | -47 |
| | VEGF-A | -12 | -132 | -37 | -8 | -137 | -48 | N/A | -103 | -42 | N/A | -81 | -38 |
| Anti-oxidant | HO-1 | 4 | 99 | 61 | 7 | 56 | 36 | N/A | 58 | 49 | N/A | 58 | 49 |
| Structural | Elastin (clinical) | 0.4 | 4 | 23 | 0.1 | -3 | 15 | N/A | -0.1 | 14 | N/A | 5 | 5 |
| | Elastin | 7 | 12 | 36 | 3 | 7 | 33 | N/A | 9 | 16 | N/A | 3 | 16 |
| | HFUS (clinical scar thickness) | 0.6 | -6 | -10 | 0.4 | -5 | -9 | N/A | -4 | -6 | N/A | -10 | -11 |
| | H+E (scar thickness) | -10 | -5 | -4 | -14 | -2 | -7 | N/A | -20 | -13 | N/A | -11 | -13 |

FIG. 12

METHOD FOR REDUCING CUTANEOUS SKIN SCARRING BY PRE-EMPTIVE PRIMING AND COMPOUNDS AND COMPOSITIONS FOR ITS IMPLEMENTATION

CROSS-REFERENCE TO RELATED APPLICATIONS

The present application is a § 371 National Stage Application of International Application Serial No. PCT/GB2021/052209, filed Aug. 25, 2021, and claims priority to United Kingdom Application Serial No. GB2013586.9, filed Aug. 28, 2020, each of which is incorporated herein by reference in its entirety.

FIELD OF THE INVENTION

This invention relates to a method for the treatment of skin to reduce the risk of developing a poor skin scarring outcome following electively induced cutaneous injury, such as following surgery or energy-based trauma to the skin derived from use of laser devices and the like, and to compounds and compositions for use in the method.

BACKGROUND OF THE INVENTION

Skin scars are the inevitable outcome of dermal tissue repair following full thickness cutaneous injury. Skin scarring in humans is an imperfect mechanism because it is a compromise made to restore tissue integrity at the expense of appearance. There is a spectrum of skin scars, ranging from stretched, depressed and/or contracted scars to raised dermal scars, such as hypertrophic and keloid scars, which are characterised by overexpression of extracellular matrix during the proliferative and remodelling phases of wound healing.

An estimated 100 million patients acquire permanent skin scars in the developed world post-elective surgery each year alone, notwithstanding those individuals undergoing elective energy-based trauma to the skin, including those undergoing elective skin trauma post-use of laser devices. Some of these skin scars may heal poorly and become clinically and pathologically abnormal by becoming symptomatic and may even develop into the aforementioned hypertrophic or keloid scars. Keloid scars are the most difficult scars to manage on the skin scarring spectrum and may even deteriorate further if treatment is attempted. Therefore, optimal evidence-based scar management is essential.

Some of the most commonly available non-invasive therapies for the treatment of scars involve topical formulations which have the advantage of localised delivery to the scar site, improved patient compliance and reduced effect of first-pass metabolism. However, most current treatment strategies of the initial steps for the management of a newly formed skin scar often adopt a watch-and-wait approach prior to commencing targeted therapy.

Catechins are a family of phenolic compounds, naturally occurring in plants, such as green and black tea, which have been shown to have antioxidant, anti-inflammatory, antiangiogenic, antiallergic, and antimicrobial effects. Various catechin compounds are found in green tea, including (-)-epicatechin (EC), (-)-epicatechin gallate (ECG), (-)-epigallocatechin (EGC) and (-)-epigallocatechin-3-gallate (EGCG), the latter being recognised as the most abundant as well as the most active catechin in relation to the aforementioned effects.

There have been various ex vivo studies into the role of EGCG in skin scarring in human skin models, where it was found inter alia that EGCG inhibited growth and induced scar shrinkage, and significantly reduced mast cell (MC) numbers. MCs have been shown to enhance acute inflammation, stimulate re-epithelialization and angiogenesis, and promote scarring.

More recently, the role of EGCG has been studied in vivo, and more specifically the concept of immediate versus delayed application of a topical formulation post-wounding has been investigated (Ud-Din et al, Journal Invest. Dermatol (2019); 139:1680-1690. e16). The objective was to deliver an active compound at the optimal time post-injury, in order to maximise its impact and improve healing. It was demonstrated that reduced scar thickness and angiogenesis, plus increased hydration and elasticity, was achieved when topical EGCG was applied immediately to the zone of injury (so-called "zonal priming") as compared with delayed application of topical EGCG two-weeks post-wounding. Such a finding was unexpected and contrary to accepted practice of commencing topical treatment only after a wound had fully re-epithelialized and a visible scar has formed.

Despite the above advances in achieving a better scarring outcome following injury through zonal priming, scarring remains a significant issue for some, long after a wound has healed, in many cases having both a physical and psychological impact on a subject. Accordingly, there remains a need for yet further improvements in scar management and it is an aim of the present invention to provide alternative and/or improved compounds, compositions and methods for optimizing cutaneous scarring outcome.

SUMMARY OF THE INVENTION

In a first aspect, there is provided a method of enhancing the quality of a scar by topical application of an agent for improving scar quality, characterised in that said agent is pre-emptively applied to a potential surgical site in advance of surgery.

The invention may also be expressed as pre-emptive use of a topical scar improving agent on a potential surgical site, in advance of surgery, to enhance the quality of the surgical scar produced.

In a second aspect, there is provided a topical agent for improving cutaneous scarring, wherein the agent is for use in pre-emptive priming of skin at a potential surgical site pre-injury.

Other expressions of the invention are set forth hereinafter and in the appended claims.

References herein to "surgery" are not only to surgical procedures involving use of mechanical cutting tools, such as scalpels, drills, burs, saws, scissors and rongeurs, but also to energy-based procedures which induce skin trauma, such as those involving the use of lasers. Accordingly, use of the term "surgery" throughout the description and appended claims should be understood to include laser surgery, particularly soft tissue laser surgery, and references to "surgical scars" include laser-induced scars, "surgical sites" include sites for laser treatment, etc.

Surprisingly, it has been discovered that pre-emptive priming of human skin pre-injury by topically applying an agent for improving scar quality at a potential surgical site provides statistically significant beneficial effects on the outcome of scarring post-surgery (including post-laser), and gives rise to superior results when compared with immediate and delayed topical application post-injury. As will be demonstrated hereinafter, the improved appearance of surgical scars by means of pre-emptive priming of skin pre-injury is achieved by reducing mast cells, angiogenesis and scar thickness, as well as increasing elastin content. Thus, it has been unexpectedly found that adopting an early intervention, namely intervention even prior to skin injury, which is opposite to the conventional “watch and wait” approach, can help minimise or substantially reduce the risk of developing a poor scar outcome.

The present invention offers significant cosmetic benefits for persons undergoing elective and/or scheduled surgery as there is an opportunity for pre-emptive priming of the skin at the proposed surgical site ahead of incision or laser treatment, and such pre-emptive priming facilitates an improved cutaneous scarring outcome for the individual. Moreover, for the millions of people worldwide that undergo such surgery each year, such early intervention reduces the risk of the resulting scar being of the abnormal (raised dermal) pathological type, such as a hypertrophic or keloid scar.

In a further aspect, the present invention provides a non-therapeutic method for enhancing the quality of a scar by topical application of an agent for improving scar quality, characterised in that said agent is pre-emptively applied to a potential surgical site in advance of surgery.

possible both to reduce scar thickness and to increase elastin content, making the scar less obtrusive as well as being softer and more malleable. Hence, the present invention offers significant improvements in the cosmetic appearance of scars, as observed post-surgery, including after laser treatment.

Topical agents for improving scar quality refer to active ingredients capable of reducing the size of the scar and/or improving the appearance thereof. Topical agents suitable for use in the present invention are preferably selected from the group comprising polyphenols. Naturally occurring polyphenols are secondary plant metabolites, and typically display anti-oxidant, anti-inflammatory and anti-microbial activity. Plant-based polyphenols of the flavonoid group are preferred, more preferably a flavan-3-ol, and most preferably a catechin. Tea is among the best sources of phenolic anti-oxidant (*Camellia sinensis* L.), especially green tea, but also black tea, oolong tea and white tea. Green tea catechins are known to have anti-oxidant and anti-inflammatory effects, and are therefore particularly suitable for use in the present invention, these being (-)-epicatechin (EC), (-)-epicatechin gallate (ECG), (-)-epigallocatechin (EGC) and (-)-epigallocatechin-3-gallate (EGCG) as shown below:

Green tea

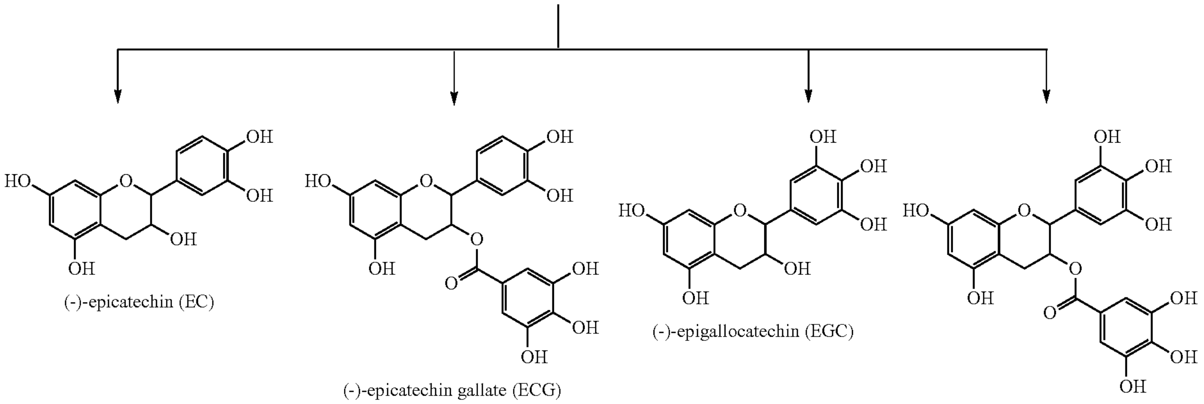

(-)-epicatechin (EC)

(-)-epicatechin gallate (ECG)

(-)-epigallocatechin (EGC)

(-)-epigallocatechin gallate (EGCG)

In another aspect, the present invention resides in a method for increasing the elastin content in the skin of a human at a site of injury by topical application of a scar enhancing agent, wherein the method comprises pre-emptive application of the agent prior to surgery.

References herein to improvements in cutaneous scarring, and enhancement of the quality of scar produced, are relative to scarring that would otherwise occur without pre-emptive topical application. In particular, it is shown that improvements and enhancements in the appearance of surgical scars are achieved by pre-emptive use of a topical agent as compared to delayed commencement once a scar has been fully formed and commencement on the day of injury itself when applied to the immediate surrounding anatomical site or zone of surgical injury (zonal priming).

Scar assessment involves the objective quantitative evaluation of a number of key parameters including inflammation and angiogenesis as well as anatomical structural features, specifically thickness and elasticity of the scar tissue. By means of the present invention, in its various aspects, it is While EGCG is the preferred polyphenol for use in the present invention, the invention is not limited to use of EGCG, and use of other polyphenols (including those derived from plants such as grapes, apples, olives, oak leaves, etc., as well as synthetic polyphenols) is within the scope of the invention.

Accordingly, and from another aspect, the present invention provides a polyphenol for use in the pre-emptive priming of human skin pre-injury to improve cutaneous scarring.

Alternatively, or in addition thereto, the invention may also be expressed as pre-emptive use of a polyphenol on a potential surgical site, in advance of surgery, to enhance the quality of scar produced.

Pre-emptive priming of the skin may commence from 1 to 15 days prior to surgery. Commencing pre-emptive priming from 3 to 7 days prior to surgery is preferred to optimise the scarring outcome. Commencing priming earlier than 7 days pre-surgery may risk non-compliance of the skin preparation regime by the individual. Thus, a treatment regime that commences from 3 to 7 days prior to surgery appears to be the optimum period to achieve an improved cutaneous scarring outcome.

The pre-emptive priming may involve topical application at least once daily for the desired period before surgery. Preferably pre-emptive priming is by twice-daily application. Topical application is continued post-surgery for a further period until localised wound inflammation resolves and scar maturation commences, typically for a period of about 2 to 10 weeks post-surgery, and preferably for a minimum of 4 to 8 weeks. As will be demonstrated hereinafter, commencing priming of the skin at a planned surgical site in advance of surgery secures a better scarring outcome than commencing priming on the day of injury (zonal priming) or post-injury.

Post-surgical application may involve use of the same or a different formulation as that applied pre-surgery. For example, the formulation applied post-surgery may include additional active ingredients to aid wound healing. Use of the same topical agent/formulation pre- and post-surgery is however preferred.

An effective amount of topical agent to be applied in the pre-emptive skin priming regime may be determined through routine experimentation; the dosage may vary according to the particular agent selected for use and the area of skin to be primed. For example, in respect of use of EGCG as topical agent, an amount of from about 150 mg to about 250 mg, preferably from 175 mg to 225 mg EGCG, may be applied to the skin once or twice daily when pre-emptively priming skin ahead of a planned (elective/scheduled) surgical incision, surgical excision, or laser surgery. Application is continued post-operatively until the scar erythema (wound inflammation) has completely subsided.

The topical agent may be supplied in a suitable carrier formulation for ease of application. For example, the topical agent may be delivered in any suitable vehicle, including but not limited to a cream, paste, lotion, gel, liquid, foam, solution, suspension, balm, spray, wax, paste or ointment.

The topical agent, and carrier formulation as appropriate, may be impregnated or otherwise incorporated in a surgical dressing for application to the site of planned surgery or laser treatment. Application by such means is advantageous since the dressing may be pre-loaded with the desired dose of topical agent and does not therefore rely on self-administration of the required dose by a subject. Moreover, the risk of the topical agent being inadvertently wiped off the skin prematurely (before being absorbed) is reduced.

Accordingly, and from another aspect, the invention also resides in a surgical dressing containing a topical agent for improving cutaneous scarring at a surgical site, wherein the dressing is for use in pre-operative application to the skin at a site of planned surgery or laser therapy. The dressing may be for use in post-operative application also.

Preferably the dressing is in the form of a dermal patch for adhesion to the skin at the planned site. The dermal patch may comprise a silicone gel sheet or other relevant material, for example, with the topical agent impregnated within the silicone gel layer or applied to the layer such that the topical agent is carried onto the skin adjacent to the scar or surrounding skin when the patch is in use. The silicone may be a pressure sensitive adhesive (PSA) or a soft skin adhesive (SSA) silicone. The dressing may be provided with a release liner which is removed to expose the adhesive silicone layer just prior to application to the planned surgical site or the site of the injury/wound. The silicone layer may optionally carry a backing sheet on the non-contact side, which may comprise a moisture-permeable layer, such as a non-woven sheet. A polyurethane backing sheet is a suitable material.

The period over which a single dressing may be worn may be optimised according to the topical agent used and the amount thereof incorporated into the dressing. For example, the dressing may be changed at least once daily, and preferably up to three times daily. Dressings according to this further aspect of the invention may be supplied to the end user in multiple dressing packs, sufficient for several weeks' application both pre- and post-surgery or laser therapy.

In one embodiment, the topical agent may be supplied in an encapsulation vehicle for enhancing penetration of the agent into the skin and optimising its performance, as well as extending shelf-life. Such an encapsulation vehicle may comprise one or more of an emulsifier/encapsulation structurant (for example, a poloxamer), a humectant (for example, glycerine and/or butylene glycol, or propylene glycol dipelargonate), a preservative (for example, phenoxyethanol), an antioxidant (for example, tocophersolan) and water. Components for aiding skin penetration of the topical agent may also be included; examples of skin penetration boosting agents include, but are not limited to, hyaluronic acid, liposomes, and cyclodextrin. Thus, many alternative formulations are contemplated for use in the method and composition of the present invention, and the use of an encapsulation vehicle is not limiting in this regard.

The preferred concentration of active topical agent in the delivery vehicle may also be determined through routine experimentation, and is within the normal expertise of a formulation chemist. Again, the concentration may vary according to the specific active ingredient selected. For example, when the active ingredient is a catechin, such as EGCG, it may be present in the delivery vehicle or carrier formulation in an amount of from about 1 to 15 mol %, preferably from about 2 to 14 mol %, most preferably from about 2.5 to 13.5 mol %.

Within the scope of this application, it is expressly intended that the various aspects, embodiments, examples and alternatives set out in the preceding paragraphs, in the claims and/or in the following description and drawings, and in particular the individual features thereof, may be taken independently or in any combination, unless otherwise stated. That is, all aspects, embodiments and/or features can be combined in any way and/or combination, unless such features are incompatible.

BRIEF DESCRIPTION OF THE DRAWINGS

The invention will now be described, by way of example only, with reference to the accompanying drawings, in which:

FIG. 12 is a table summarising the percentage differences in the immunohistochemical data between placebo and EGCG treated arms over the testing period.

DETAILED DESCRIPTION OF THE INVENTION

All references cited herein are incorporated by reference in their entirety. Unless otherwise defined, all technical and scientific terms used herein have the same meaning as commonly understood by one of ordinary skill in the art to which this invention belongs.

The invention will now be illustrated, by way of non-limiting example only, by reference to a study undertaken to demonstrate the effects of pre-emptive priming on the outcome of scarring as compared with zonal priming at a wound site and treatment after scar formation. Various modes of topical application were evaluated in a well-established human skin scarring model to identify that pre-emptive priming pre-injury had a greater impact on scarring outcome compared to day of- or post-injury application.

Figure 1:
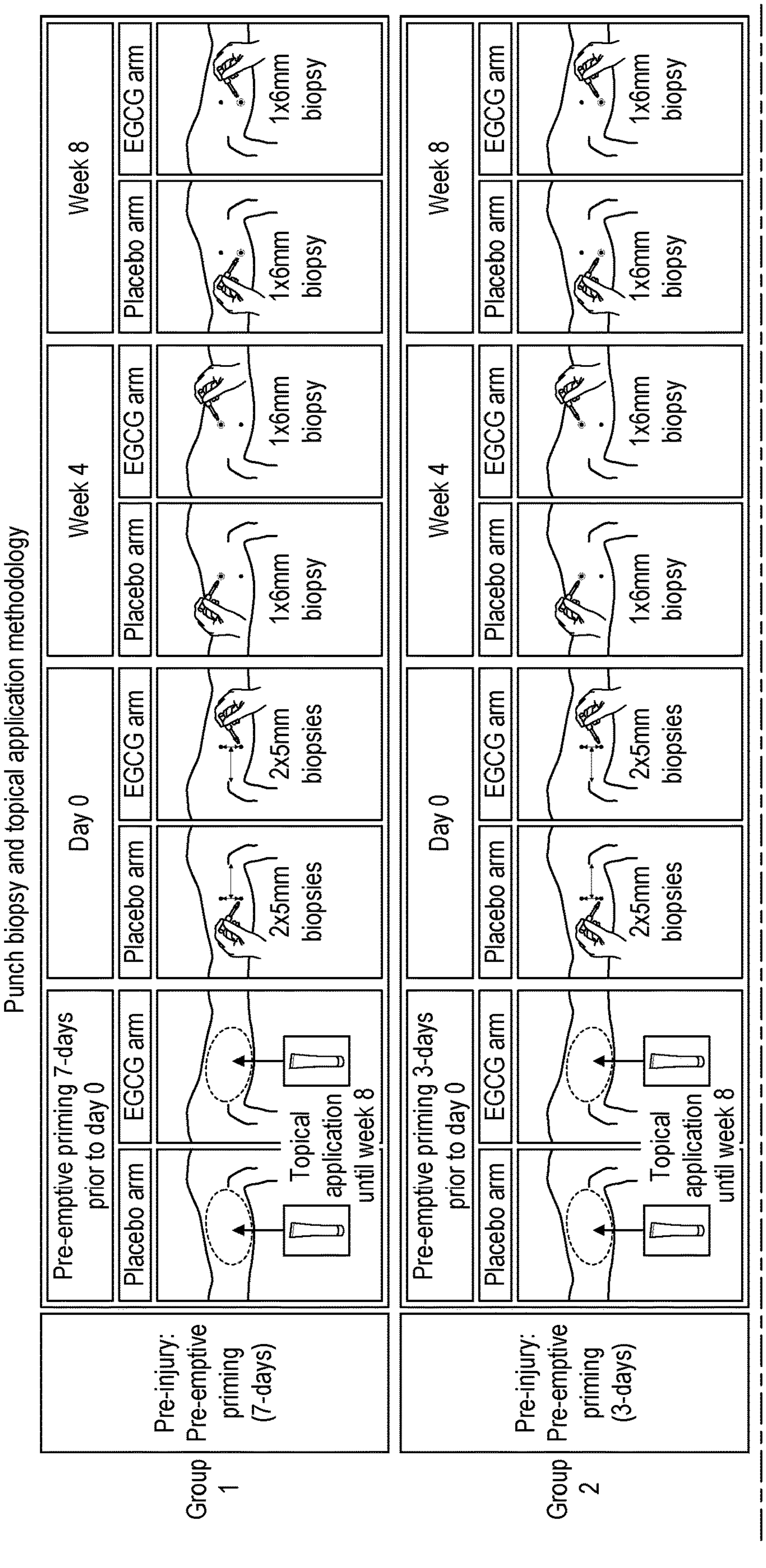
FIG. 1 is a diagrammatic representation of the punch biopsy methodology used in a study to determine the effects of pre-emptive priming.
Figure 1:
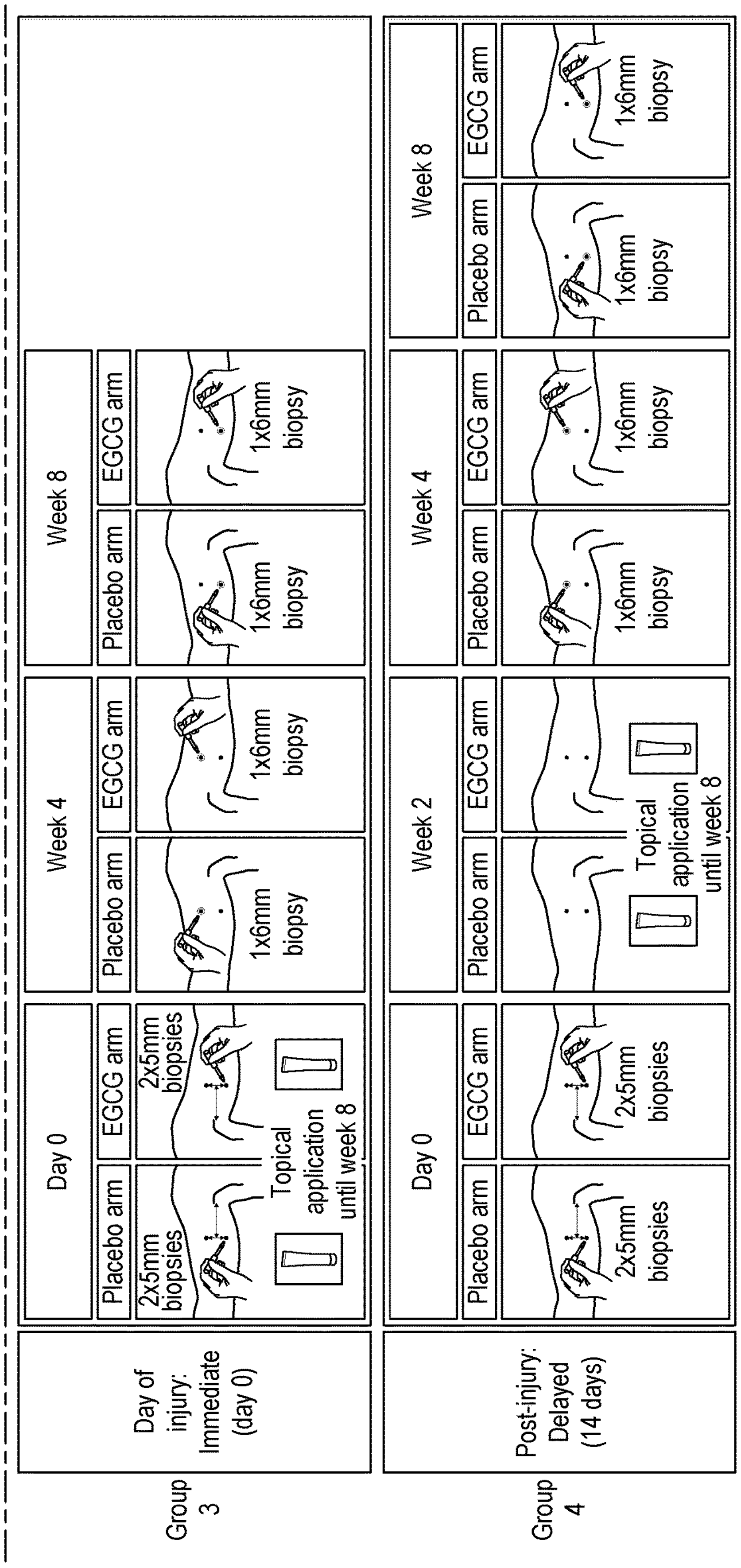

A double-blind randomized placebo-controlled trial was conducted using a temporal punch-biopsy model. The punch biopsy and topical application methodology used in the study is illustrated in FIG. 1, namely showing pre-injury pre-emptive priming (7-days), pre-injury pre-emptive priming (3-days), day of injury (immediate application on day 0), post-injury (delayed 2 weeks post injury) including biopsy time points and time of topical applications. Each group applied both placebo and topical formulations twice daily for the duration of the study until week 8, with only the starting time point differing between groups Participants were split into 4 groups (n=10 in each group) in order to compare different modes (timings) of commencement of the topical application:

Group-1: Pre-emptive Priming (7-days): pre-injury

Group-2: Pre-emptive Priming (3-days): pre-injury

Group-3: Immediate (0-day): day-of-injury

Group-4: Delayed (14-days): post-injury

Clinical quantitative devices were used to objectively monitor cutaneous healing at weekly intervals and punch biopsies were performed on day 0 (uninjured skin) and at weeks 4 and 8 for protein and gene expression analyses. In the trial, topical EGCG and a placebo topical were applied twice daily for the duration of the trial until week 8 with only the starting time points differing between groups.

Figure 2:
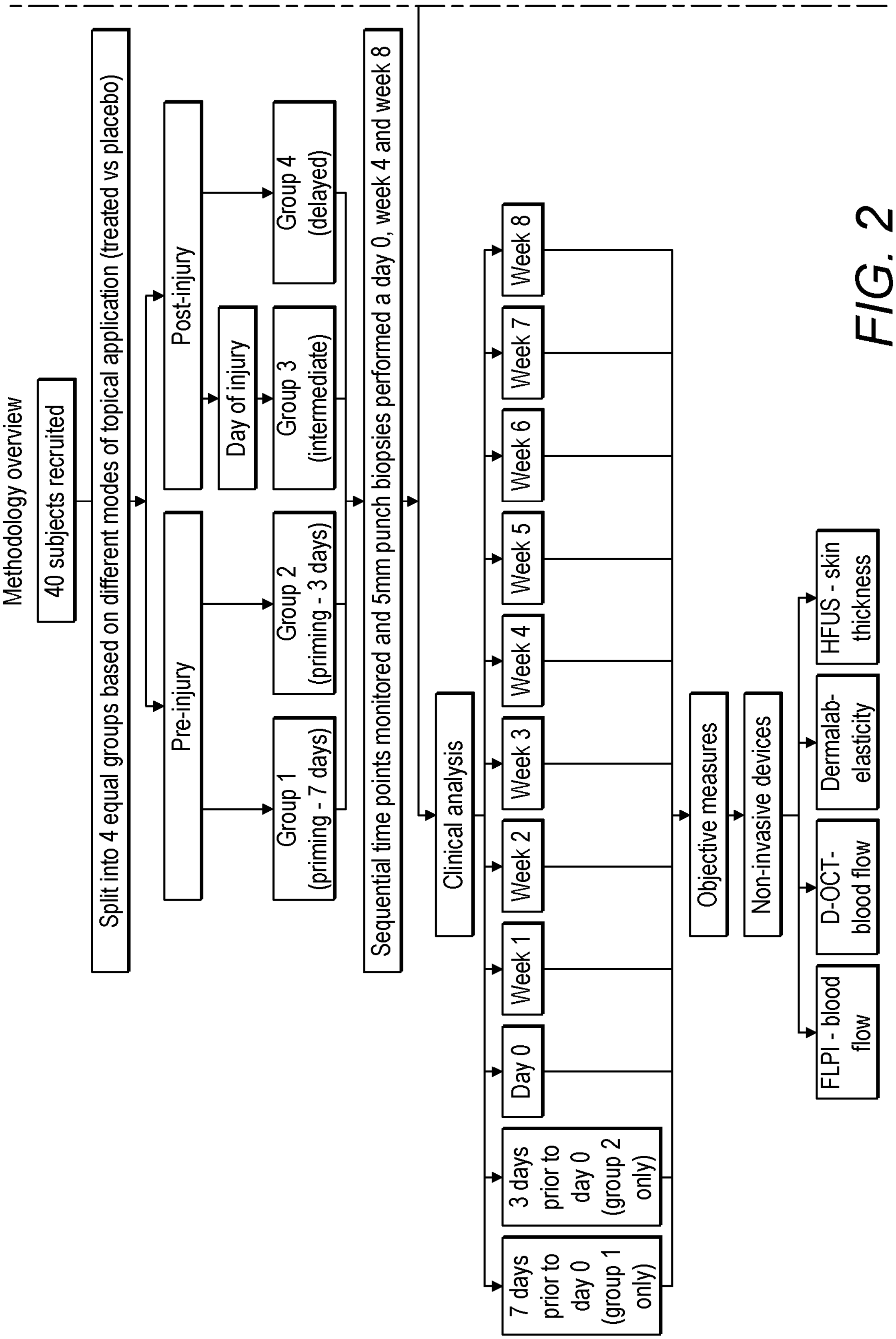
FIG. 2 is a methodology overview showing the clinical and experimental analysis conducted in the study.
Figure 2:
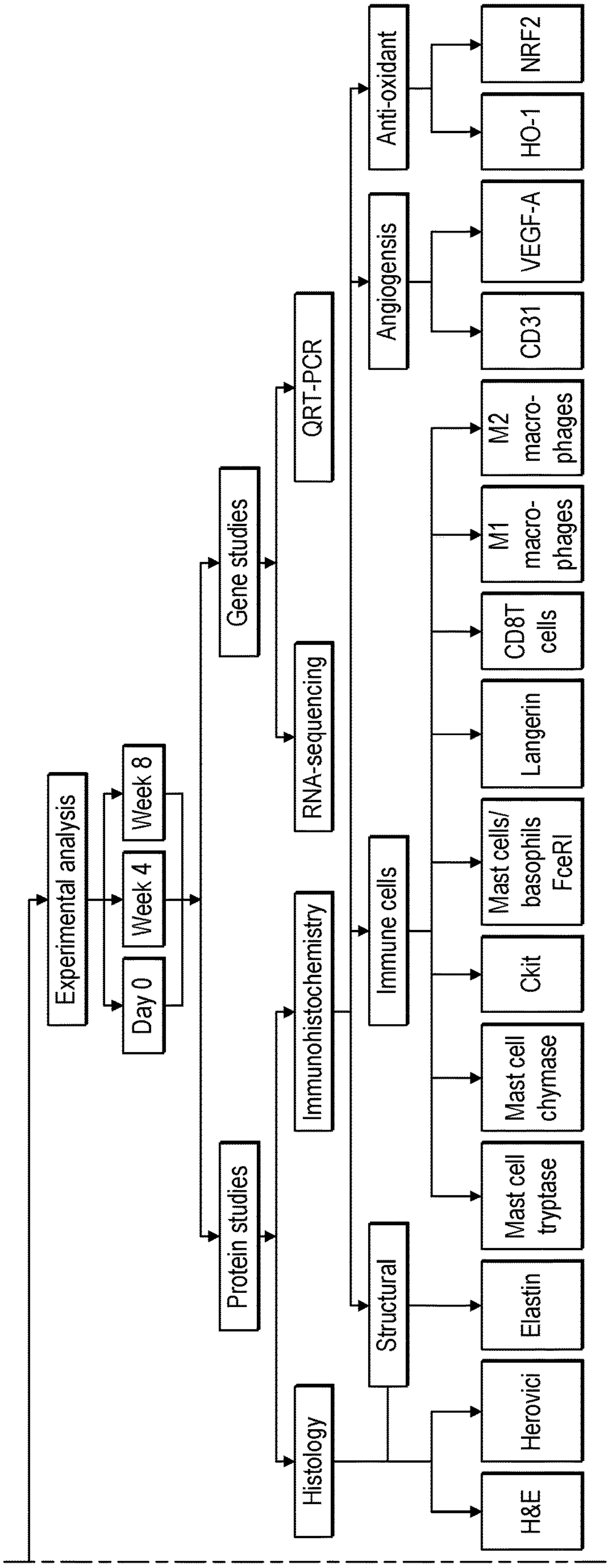

An overview of the methodology used in the study is provided at FIG. 2 including both the pre-injury priming versus immediate and post-injury timing of the topical application modalities, study time points and the non-invasive and invasive measures used.

Clinical and experimental analysis involved use of non-invasive devices as well as protein and gene studies. Excisional skin biopsies in upper arms were evaluated weekly with multiple quantitative devices over an 8-week period. Immunohistochemical analyses, mRNA sequencing and QRT-PCR were performed on tissue biopsies.

Mast Cells

The strong association of mast cells (MC) with skin scarring and fibrosis is well-established. MCs have been shown to enhance acute inflammation, stimulate epithelialization and angiogenesis, and promote scarring.

It is known that continuous inflammation can stimulate the secretion of pro-inflammatory cytokines which can lead to excessive scarring such as hypertrophic and keloid scar formation. It has been shown that EGCG has an inhibitory effect on several key markers including langerin, FcεRI and several mast cell markers. Mast cells affect fibroblasts present in the remodelling phase of healing, and thus affect regulation of scar formation. Indeed, mast cell expression increases in normortrophic and hypertrophic skin scars compared to normal skin and this increases with scarring severity. Blocking mast cell function is therefore believed to be desirable in the quest to minimise or prevent excessive scarring. Accordingly, the effect of pre-emptive use of EGCG on MCs was investigated.

Figure 3A:
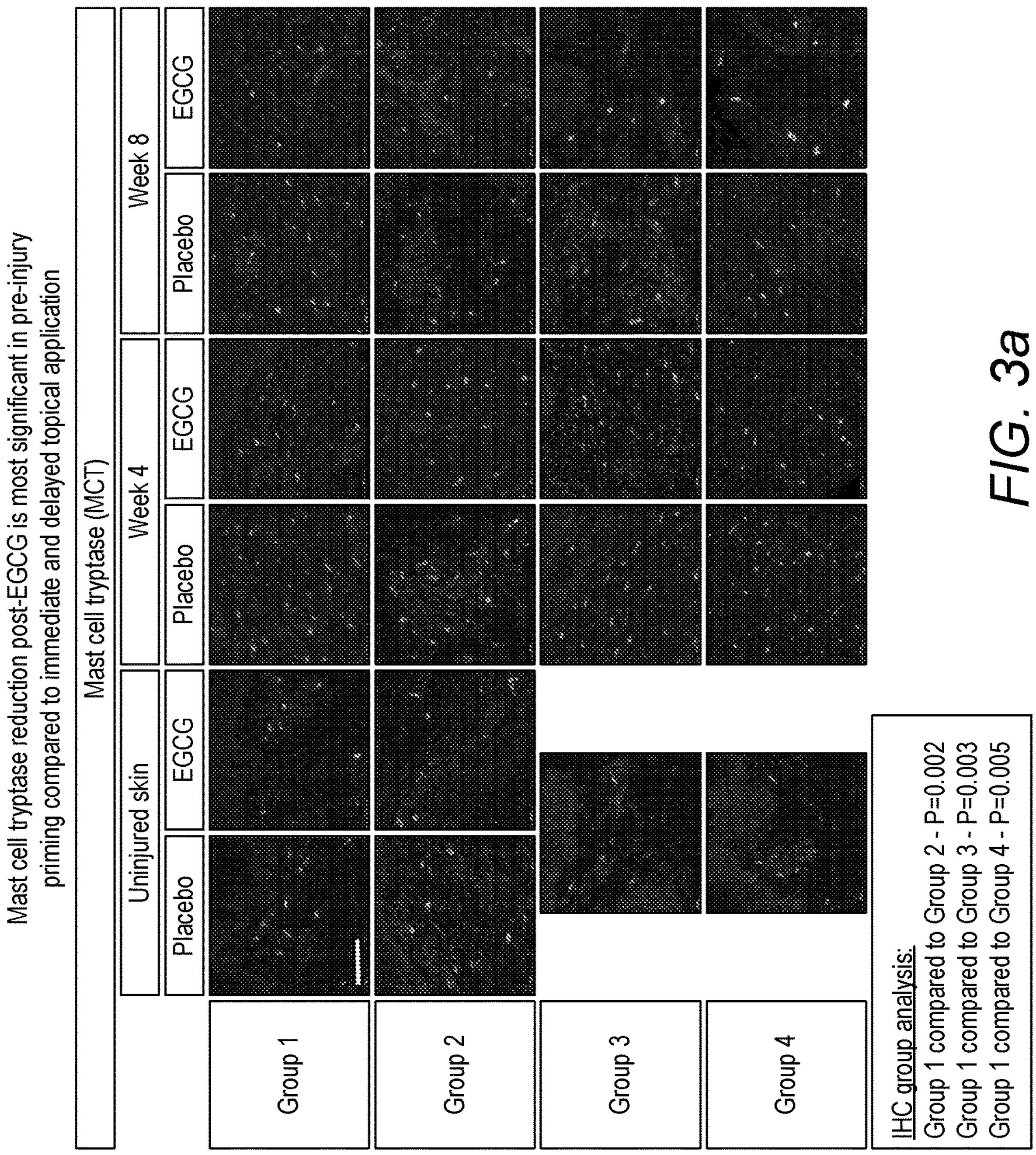
FIGS. 3*a*, 3*b* and 3*c* show a mast cell analysis comparing the use of EGCG versus a placebo, respectively mast cell tryptase (MCT) immunohistochemical marker images (FIG. 3*a*), mast cell chymase (MCC) immunohistochemical marker images (FIG. 3*b*) and CKit staining images (FIG. 3*c*)
Figure 3B:
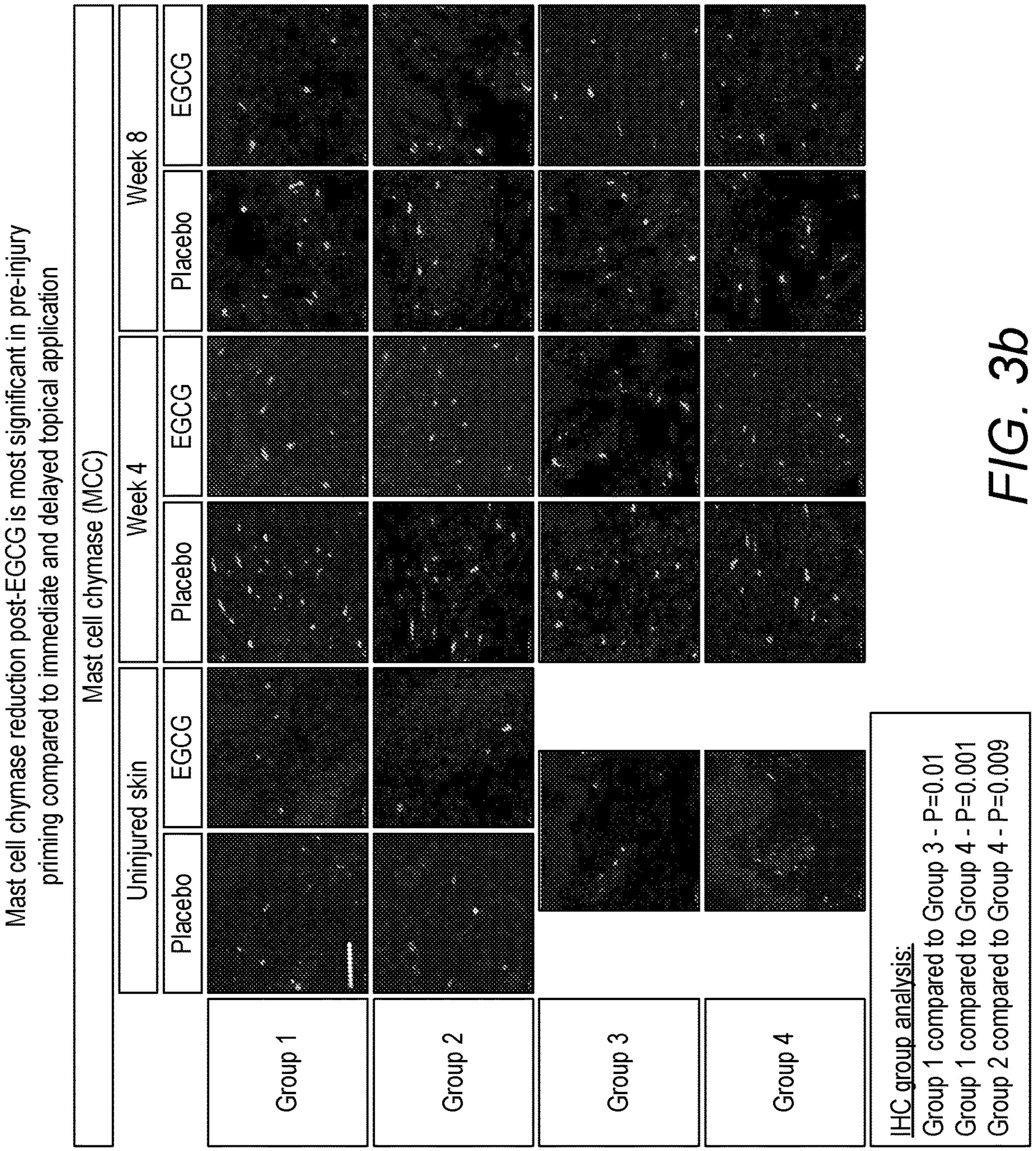
Figure 3B:
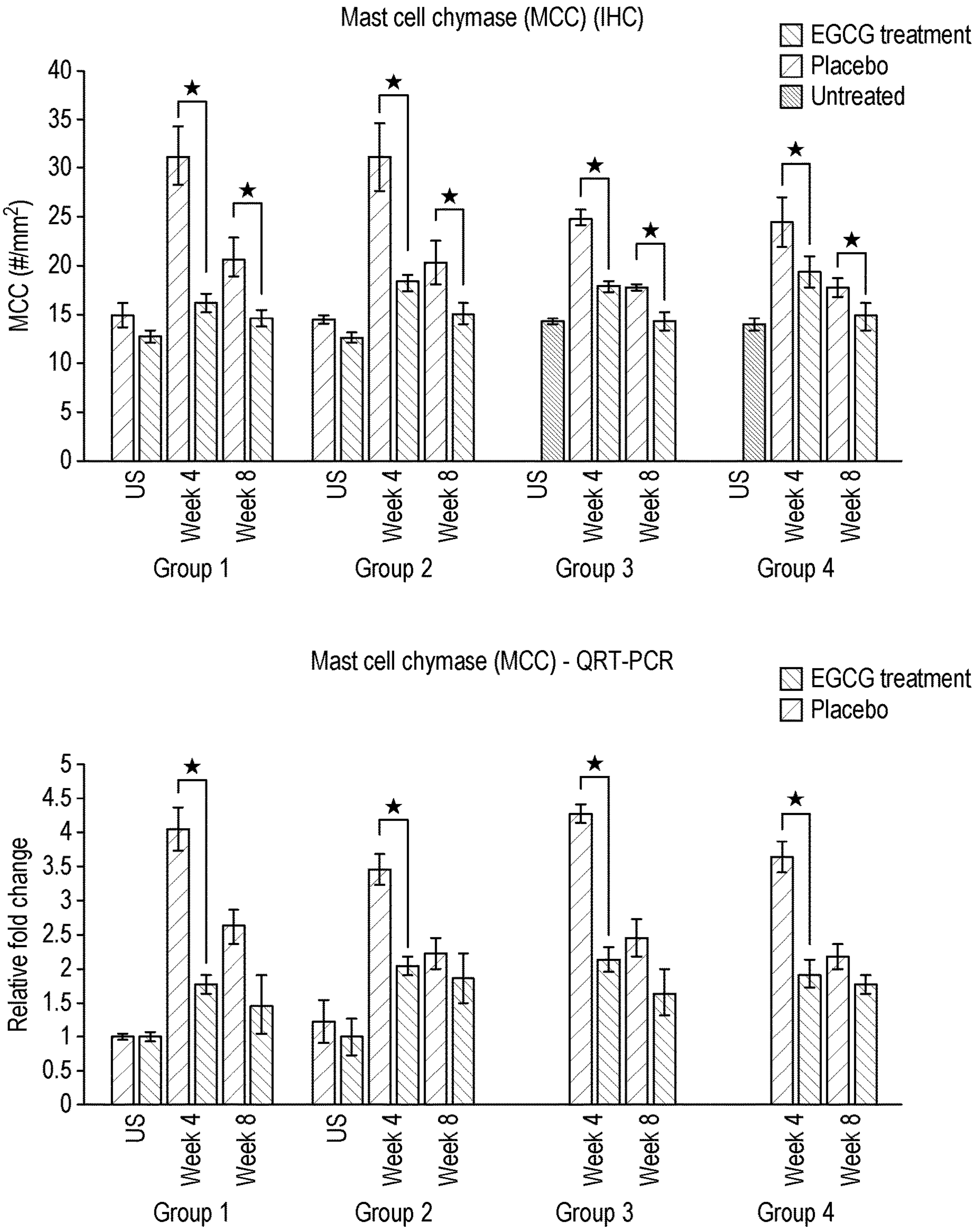
Figure 3C:
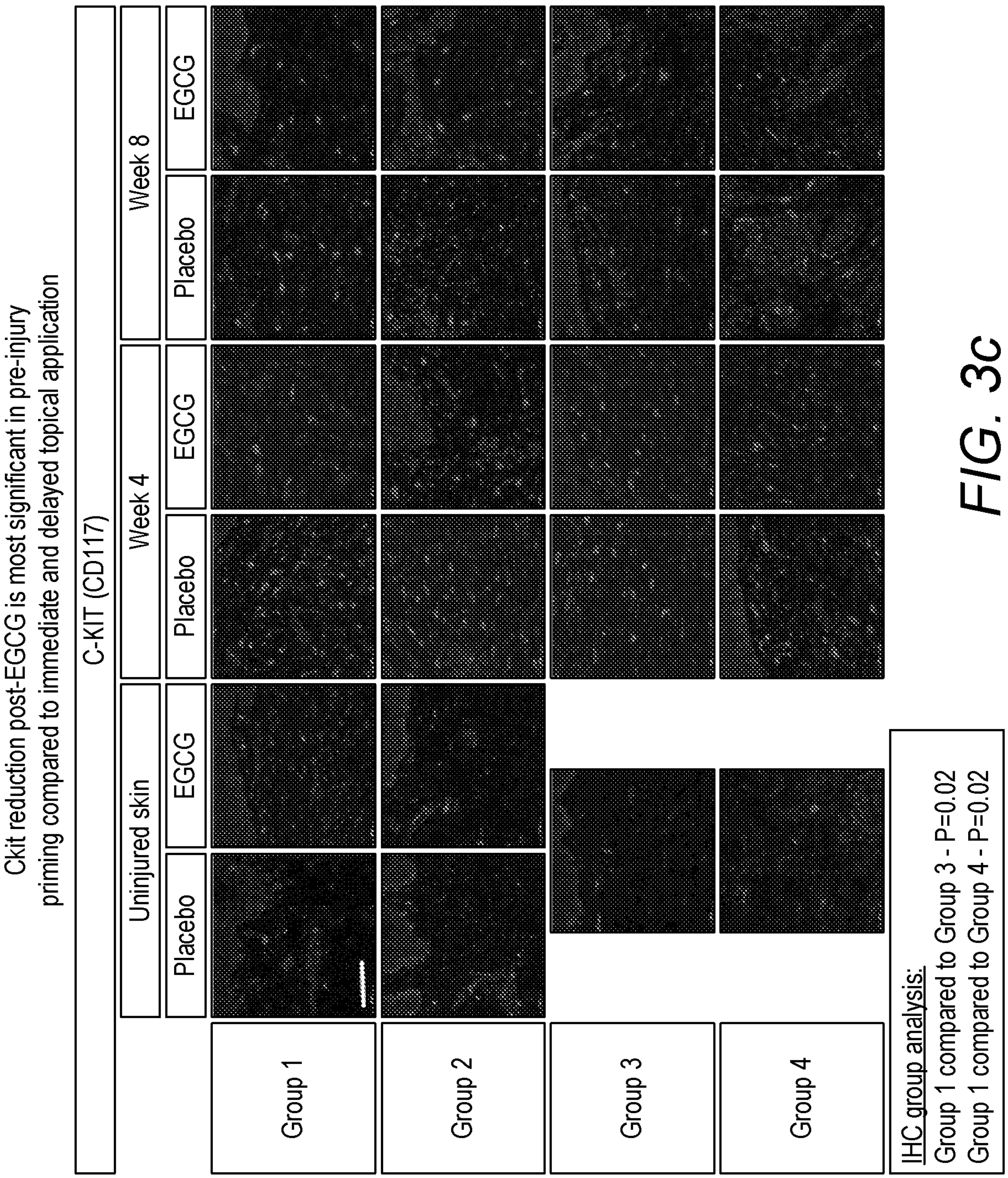
Figure 3C:
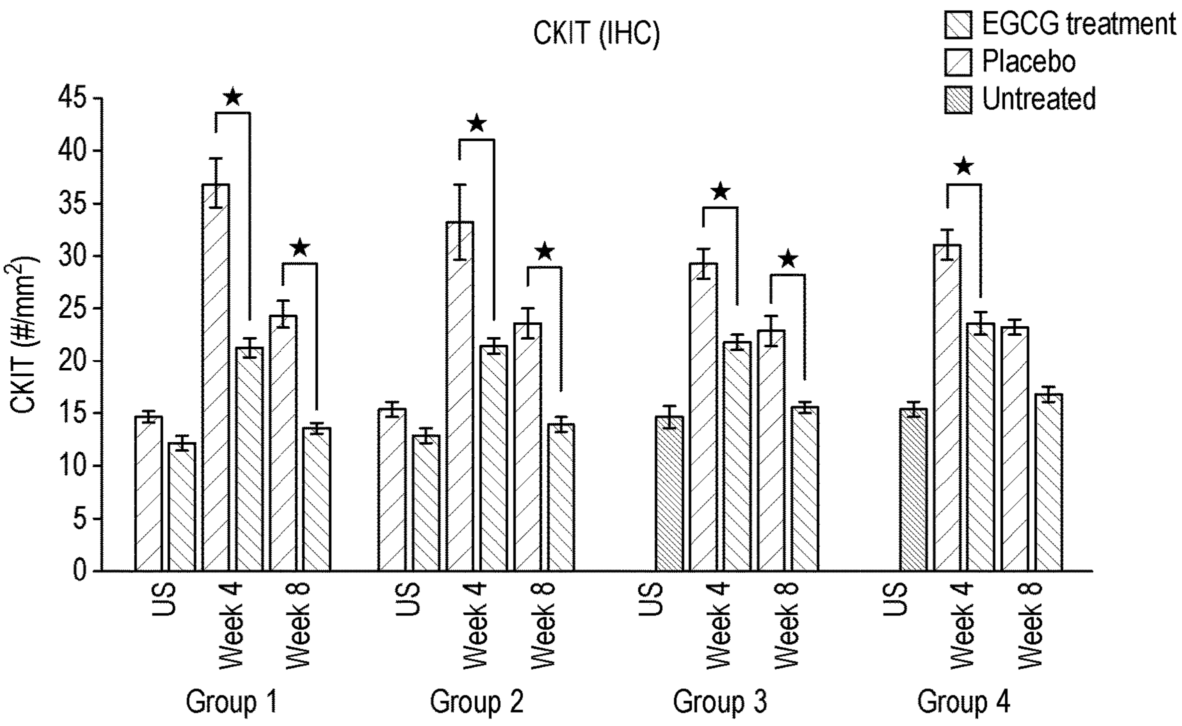

MC identification was performed using mast cell tryptase (MCT), mast cell chymase (MCC) and CKit markers. As will be seen from FIGS. 3*a*, 3*b* and 3*c*, all three markers demonstrated that EGCG-treated scars had significantly fewer positive cells at weeks 4 and 8 compared to placebo-treated scars ($p<0.01$) for all groups. Further analysis showed differences between the groups in relation to MC reduction. MCT analysis demonstrated a significant difference between groups at week 4 ($p=0.001$) and the pre-emptive priming group-1 was superior. The percentage differences between the change in placebo and EGCG for group-1 compared to group-2 was 58% ($p=0.002$), group-3 was 53% ($p=0.003$) and group-4 was 52% ($p=0.005$). MCC showed a significant difference at week-4 between groups ($p=0.001$). Group-1 had a greater difference than group-3 by 29% ($p=0.01$), group-4 by 41% ($p=0.001$), and group-2 had a larger difference than group-4 by 29% ($p=0.009$). CKit analysis further demonstrated a significant difference between the groups at week-4 ($p=0.01$). The greatest difference was in group-1 compared to group-3 by 26% ($p=0.02$) and group-4 by 27% ($p=0.02$). Subsequent QRT-PCR analysis further confirmed down-regulation of MCT and MCC ($p<0.05$) in EGCG-treated samples at week-4 in all groups. MCT, MCC and CKit quantitative measurements are expressed in $mm^2$.

Thus, it is seen that MC reduction post-application of EGCG is most significant in pre-injury priming compared to immediate and delayed topical application.

Langerin and Fc epsilon RI Cells

Figure 4:
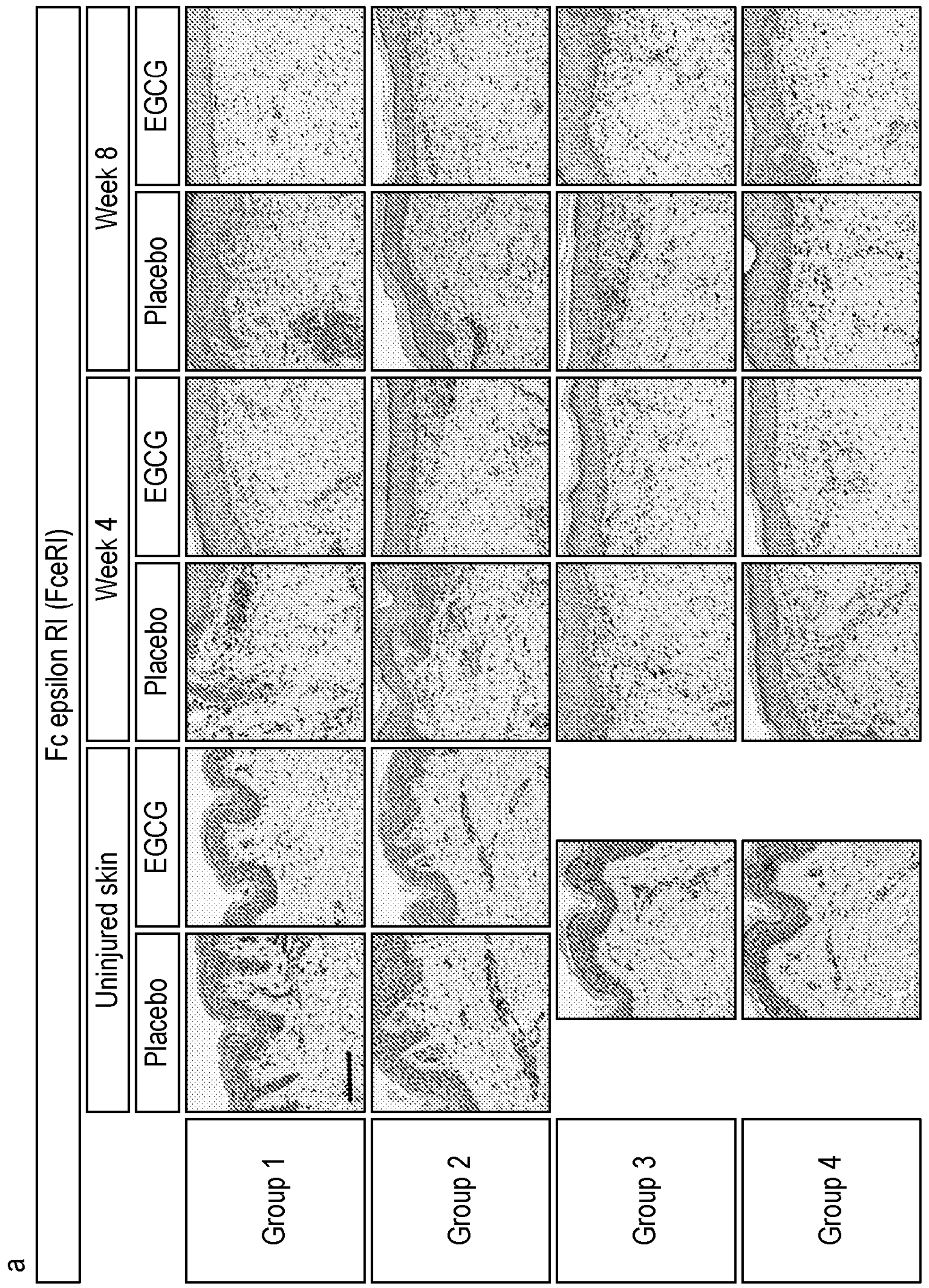
FIG. 4 shows marker images for Fc epsilon RI comparing the use of EGCG versus the placebo.
Figure 4:
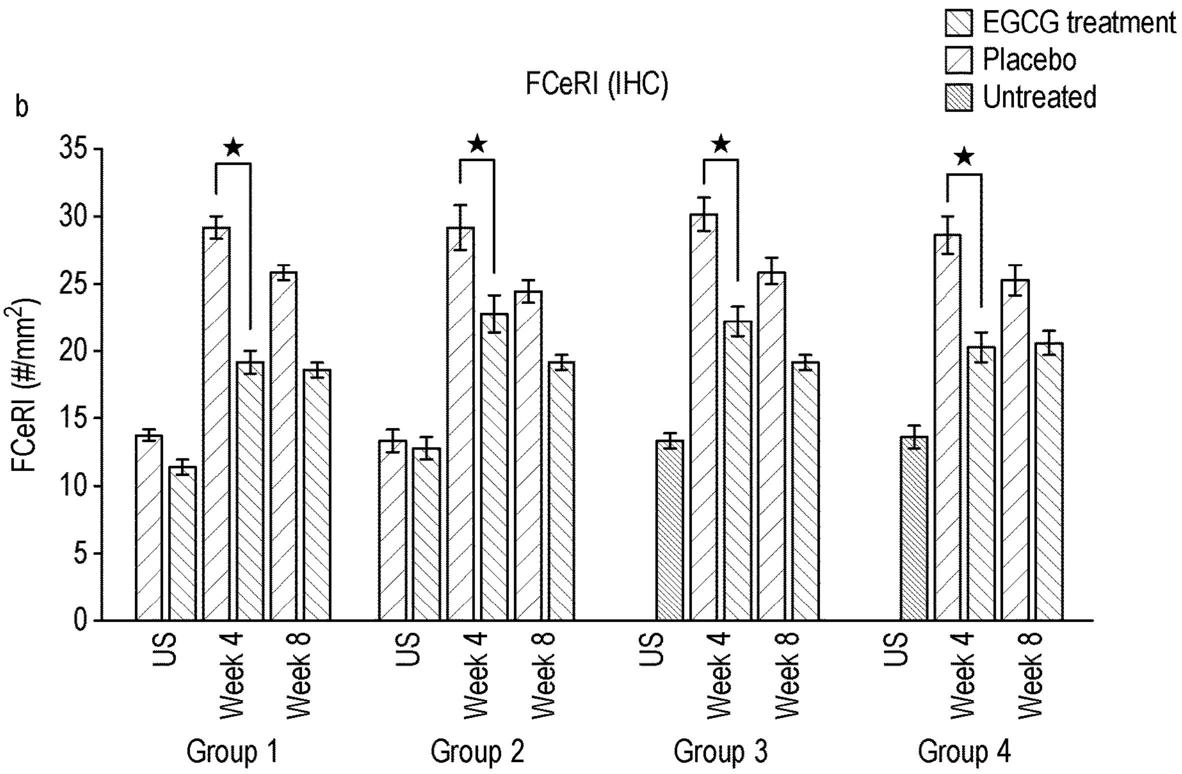
Figure 5:
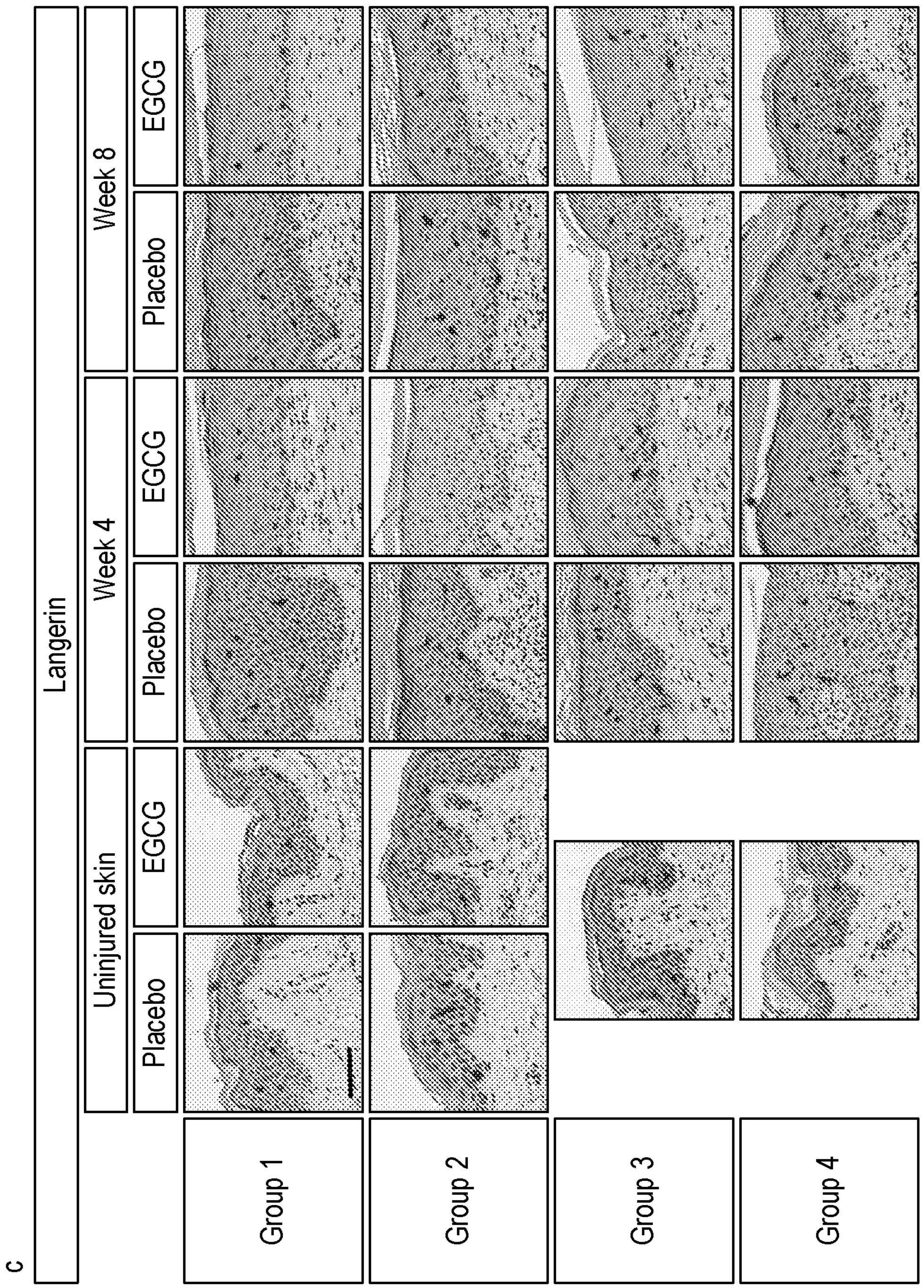
FIG. 5 shows marker images of langerin comparing the use of EGCG with the placebo.
Figure 5:
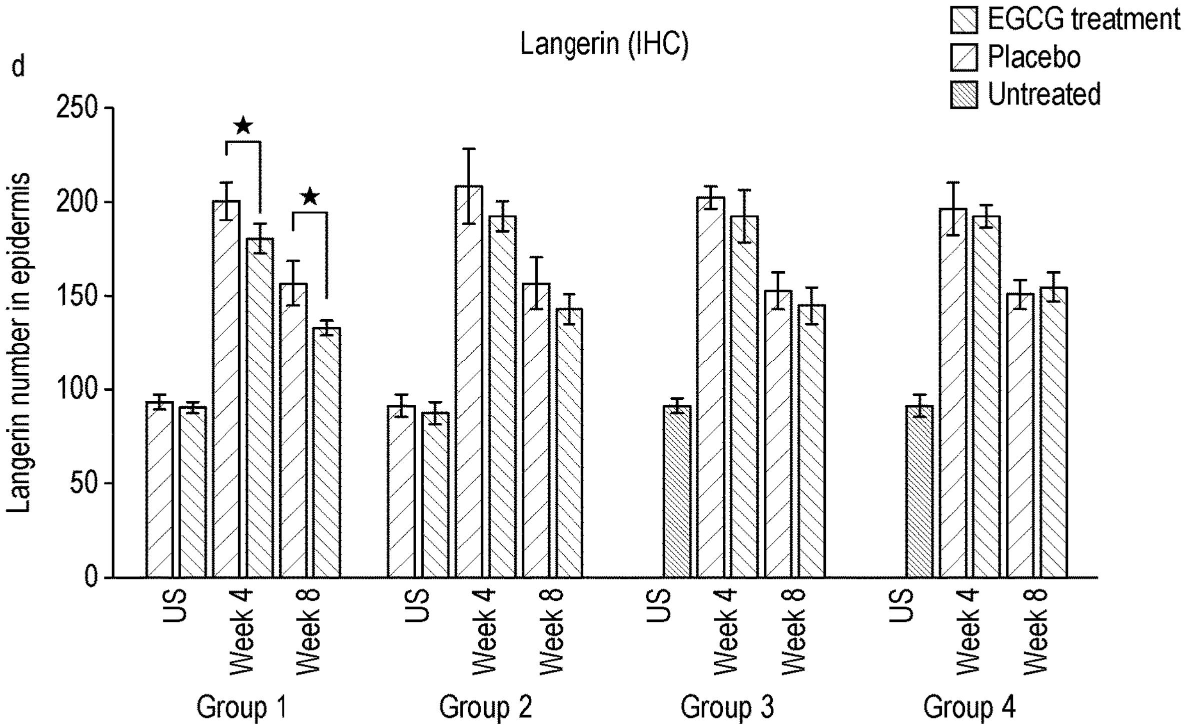

Analysis of several further markers to identify if EGCG had any effect on other cell types including Fc epsilon RI (FcεRI), langerin, M1 and M2 macrophages and CD8 T-cells was performed. As seen from FIG. 4 there were greater levels of FcεRI in scar tissue compared to uninjured skin predominantly at scar edges and less centrally, and this was highest at week-4 in all groups. There was a significant reduction in FcεRI at week-4 in EGCG-treated samples compared to placebo in all groups ($p<0.01$). As seen from FIG. 5, langerin analysis demonstrated a significant 13% reduction in EGCG-treated samples compared to the placebo samples at week-4 in group-1 only ($p=0.02$). Thus langerin reduction was most significant in pre-injury priming.

Blood Flow

Figure 6A:
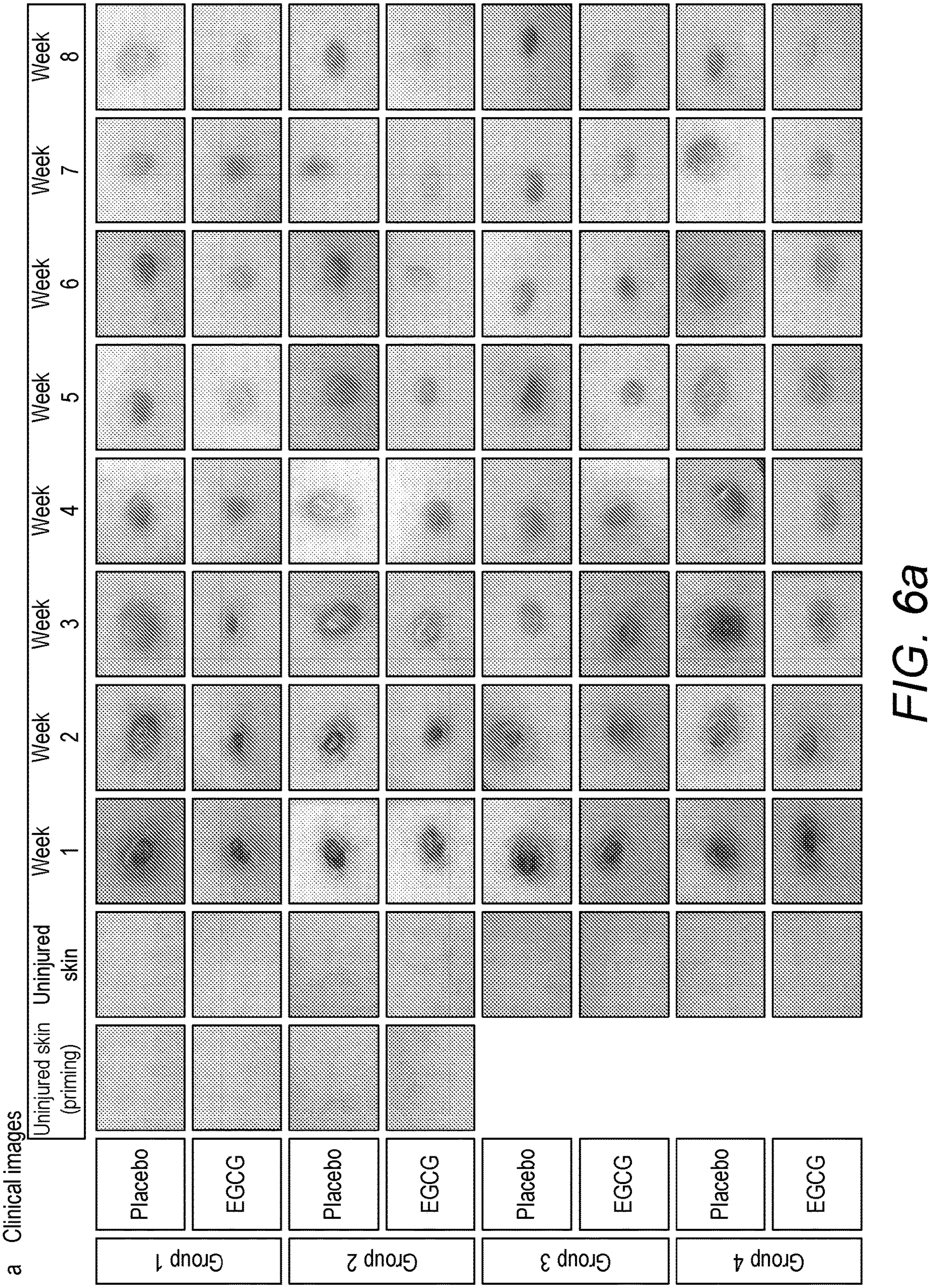
FIGS. 6*a*, 6*b* and 6*c* show clinical images, corresponding full-field laser perfusion images (FLPI) and dynamic optical coherence tomography (D-OCT) images respectively.
Figure 6B:
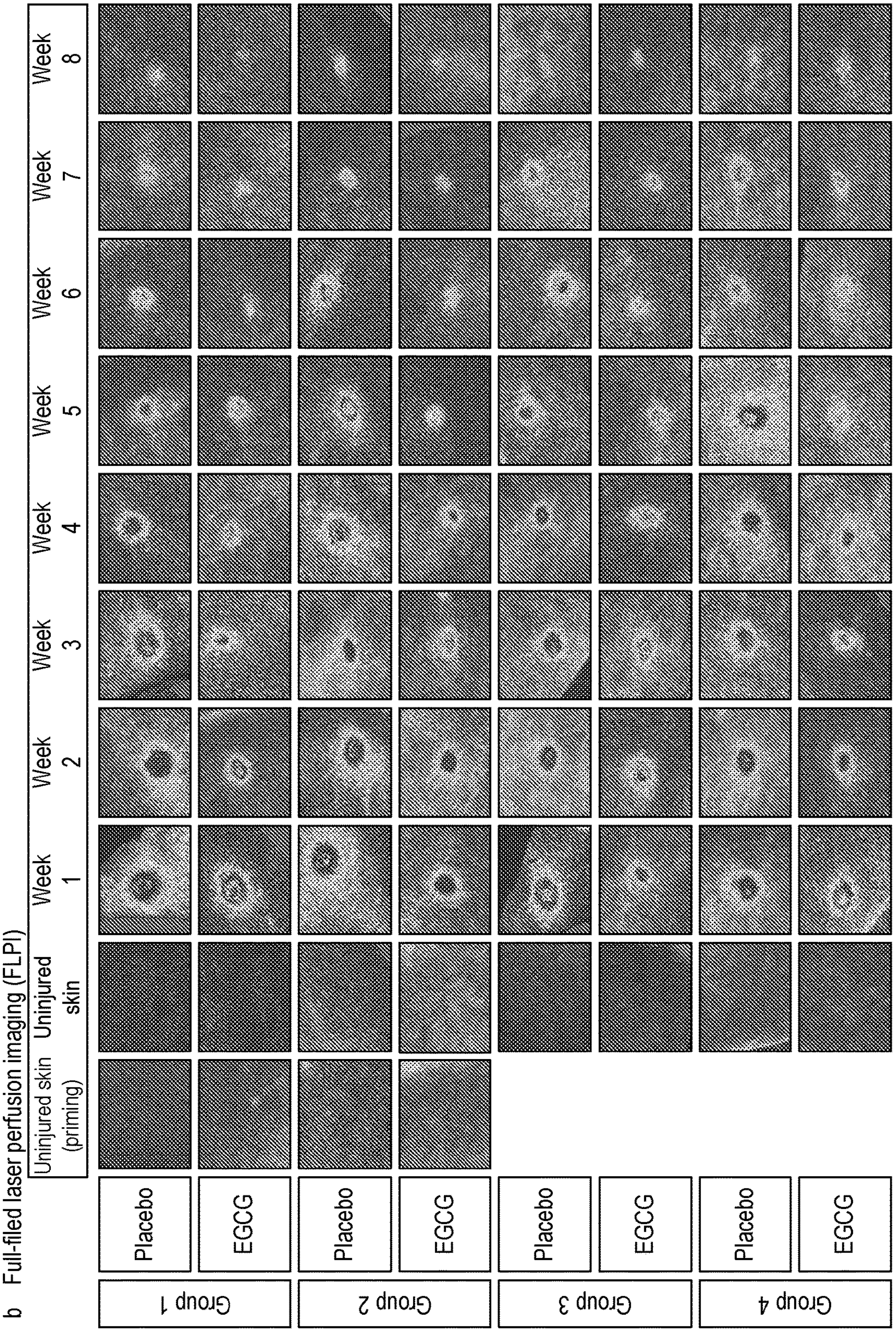
Figure 6B:
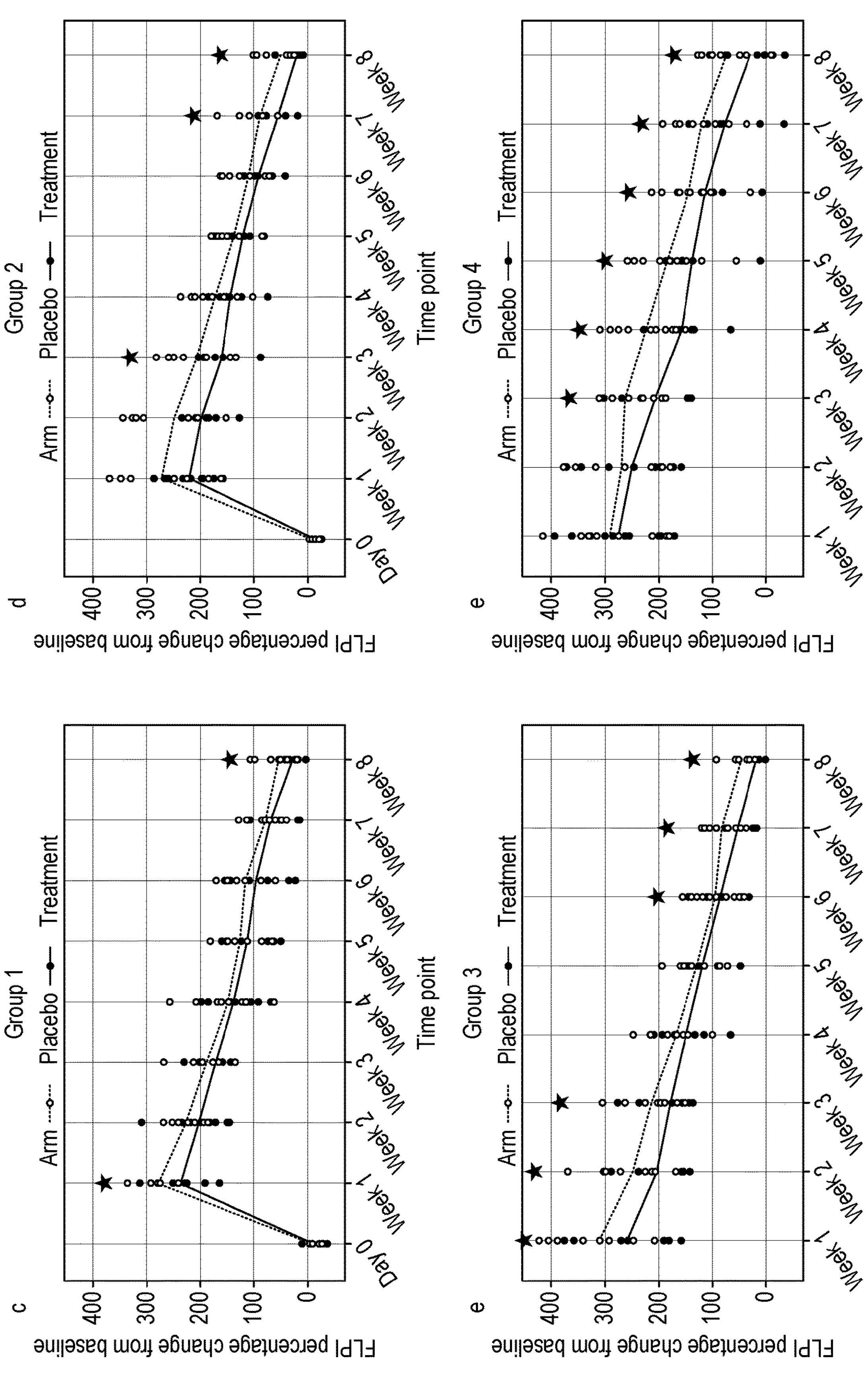
Figure 6B:
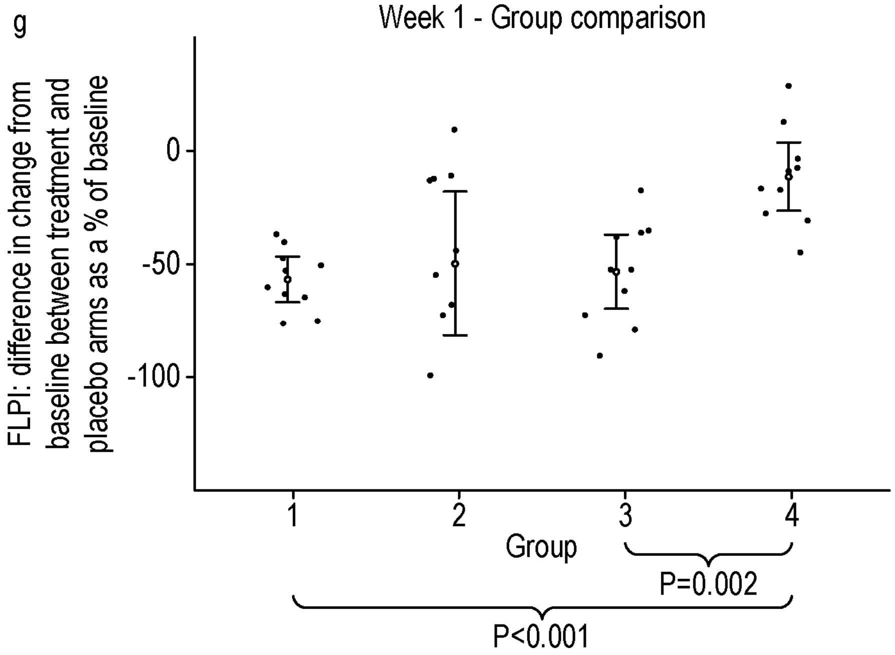
Figure 6C:
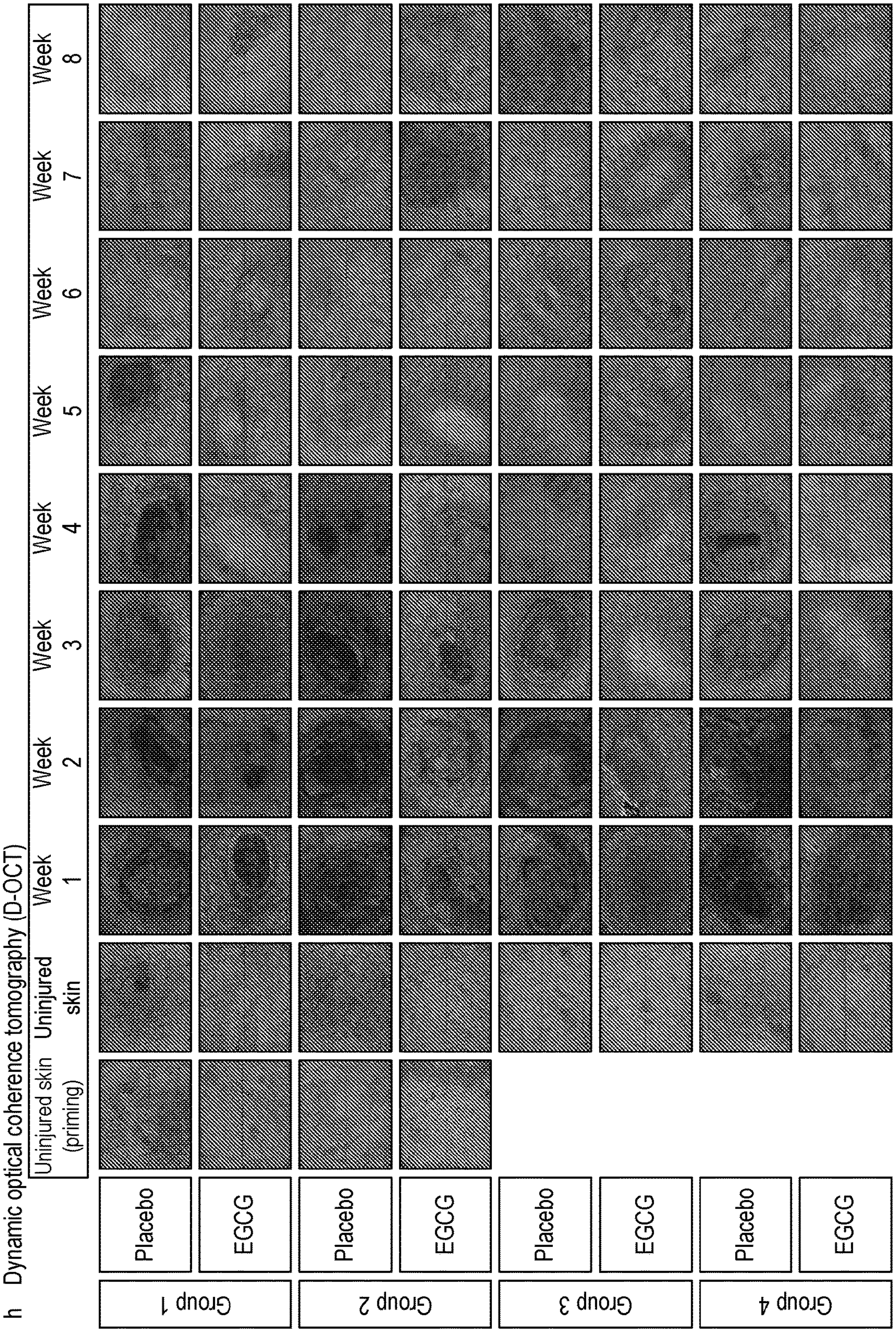
Figure 6C:
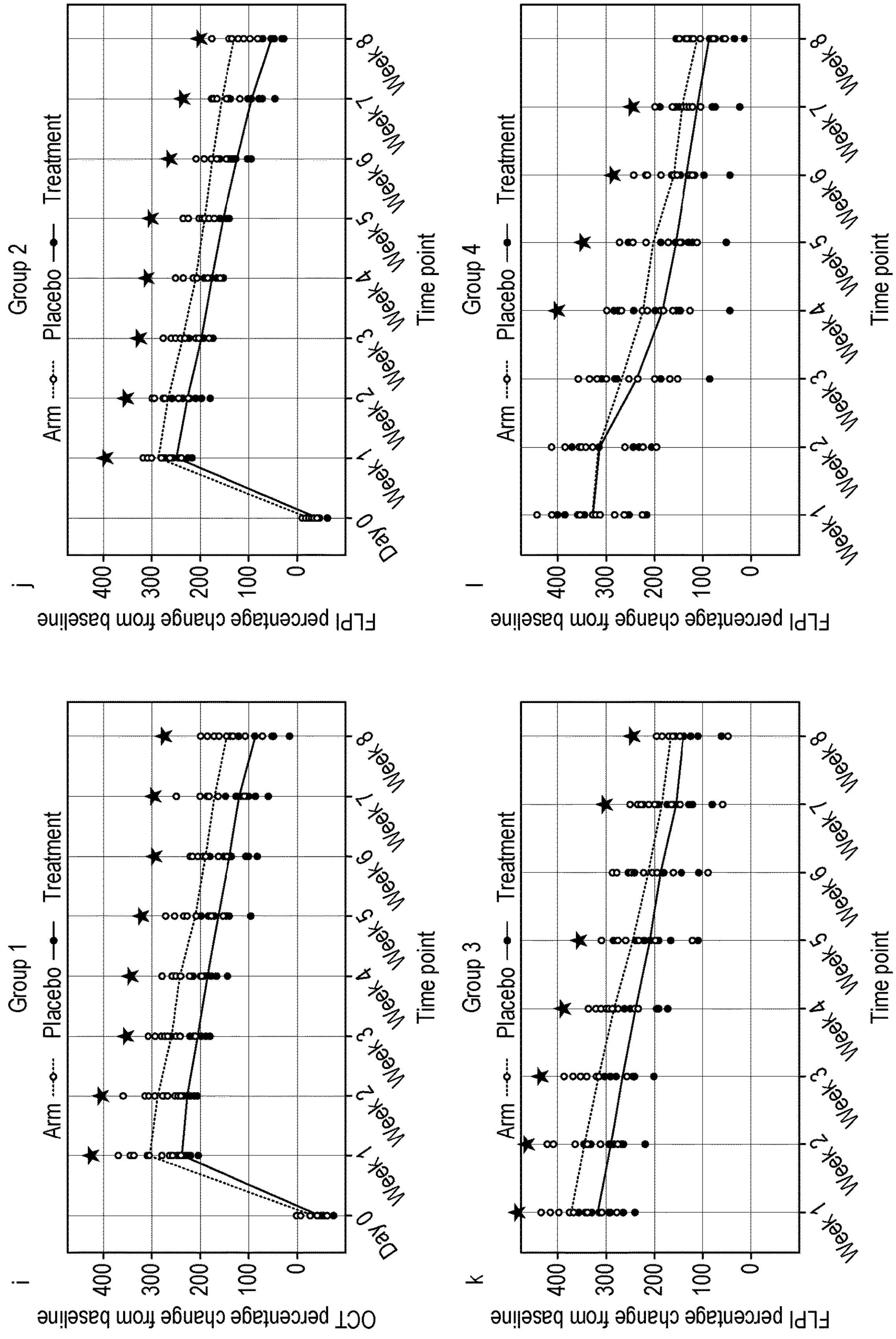
Figure 6C:
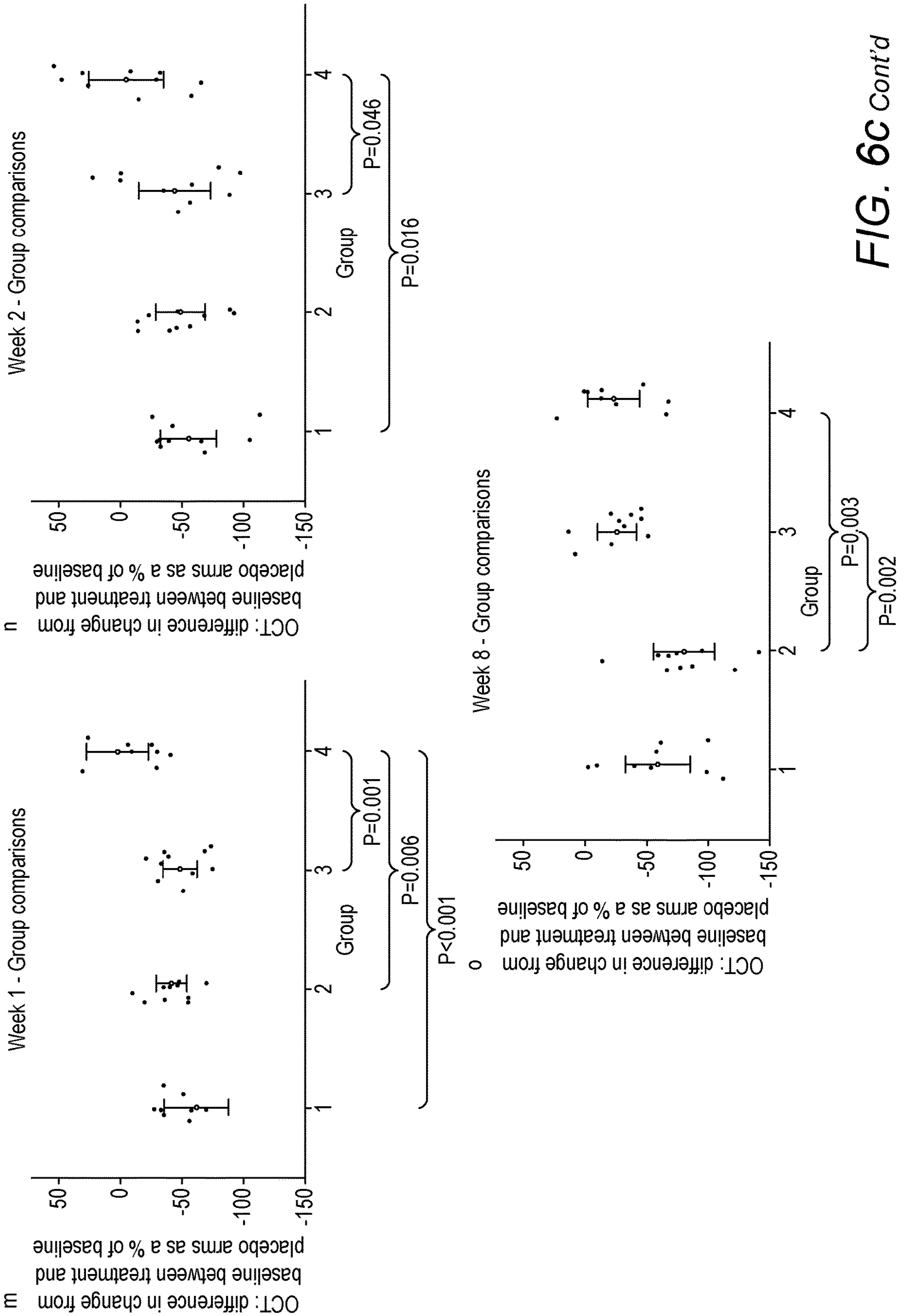

Blood flow analysis using non-invasive objective measures, including full-field laser perfusion imaging (FLPI) and dynamic optical coherence tomography (D-OCT), was undertaken. Clinical images and the corresponding FLPI and D-OCT images are shown in FIGS. 6*a*, 6*b* and 6*c* respectively.

FLPI measurements showed that blood flow progressively reduced over 8-weeks from baseline in all groups and in treated and placebo arms. There was a significant reduction in EGCG arms compared to placebo arms across all groups; group-1 at weeks-1 and 8 ($p<0.01$), group-2 at weeks-3, 7 and 8 ($p<0.01$) group-3 at weeks 1-3 and 6-8 ($p<0.01$) and group-4 was significantly reduced at weeks 3-8 ($p<0.01$). Between group comparison analysis showed that groups-1 and 3 reduced blood flow more than group-4 at week-1 ($p<0.001$, $p=0.002$ respectively).

D-OCT analysis of blood flow also demonstrated a reduction over time in both arms and in all groups. This was significantly decreased in the EGCG-treated compared to the placebo; group-1 at weeks 1-8 ($p<0.01$) and group-2 at weeks 1-8 ($p<0.01$), group-3 at weeks 1-5, 7 and 8 ($p<0.01$) and group-4 at weeks 4-7 ($p<0.01$). Group comparison analysis demonstrated that groups 1-3 reduced blood flow more than group-4 at week-1 ($p<0.001$, $p=0.006$, $p=0.001$ respectively). Priming Group-1 had a greater difference than group-4 at week-2 ($p=0.016$), whilst group-2 reduced more than groups-3 and -4 at week-8 ($p=0.003$, $p=0.002$ respectively).

Thus, a significant reduction in blood flow was observed in pre-injury priming.

Angiogenic Markers mRNA sequencing analysis demonstrated in group-1, the most significantly differentially expressed genes which were reduced with EGCG compared to placebo were haemoglobin subunit beta (HBB), haemoglobin subunit alpha-1 (HBA1) and haemoglobin subunit alpha-2 (HBA2) at week-4. In order to further support these findings and the clinical findings, two well-known and established angiogenic immunohistochemical markers; CD31 and VEGF-A were used.

Figure 7A:
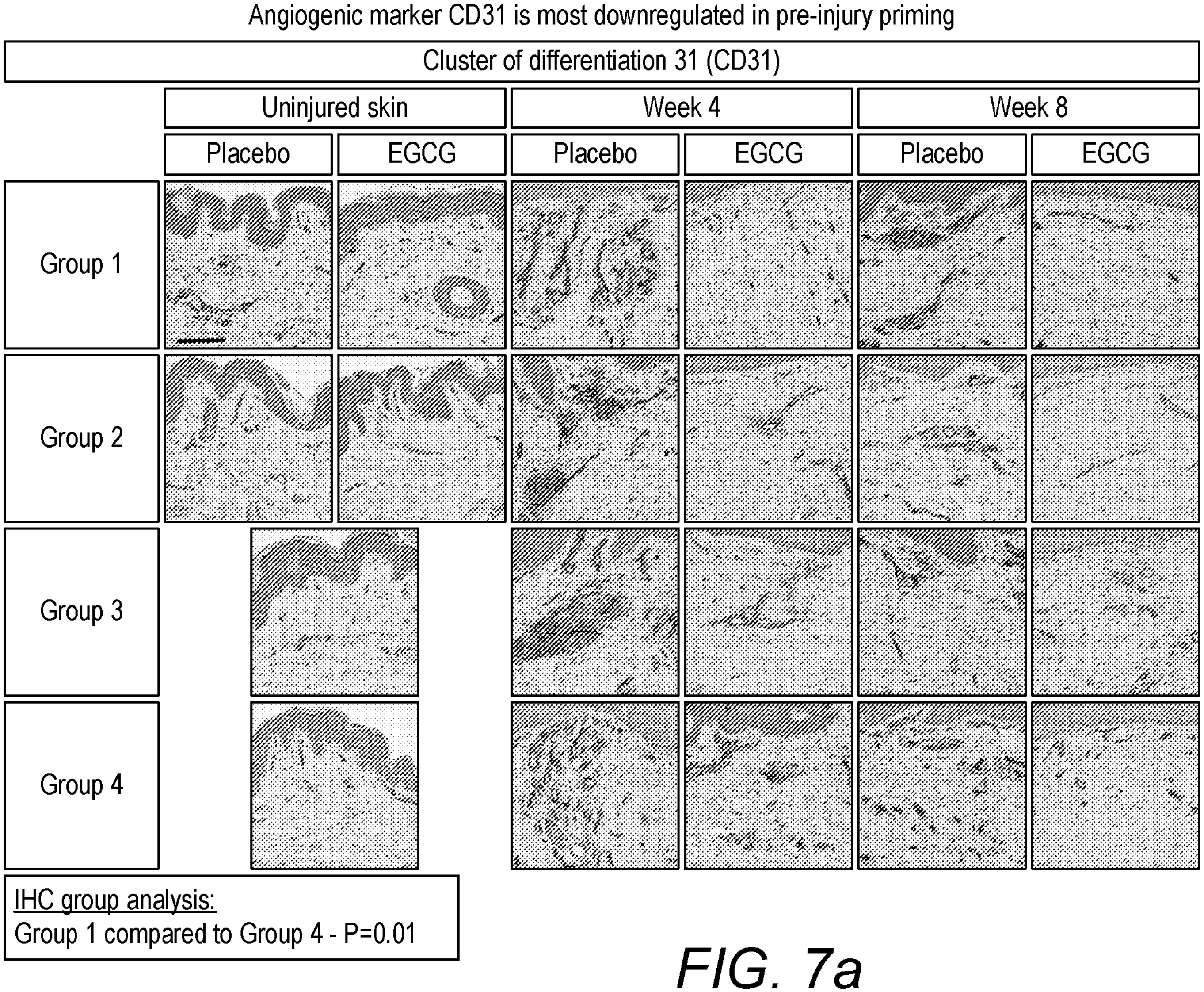
FIGS. 7*a* and 7*b* show angiogenesis marker analysis comparing the use of EGCG with the placebo by means of Cluster of Differentiation 31 (CD31) images and Vascular Endothelial Growth Factor A (VEGF-A) images.
Figure 7A:
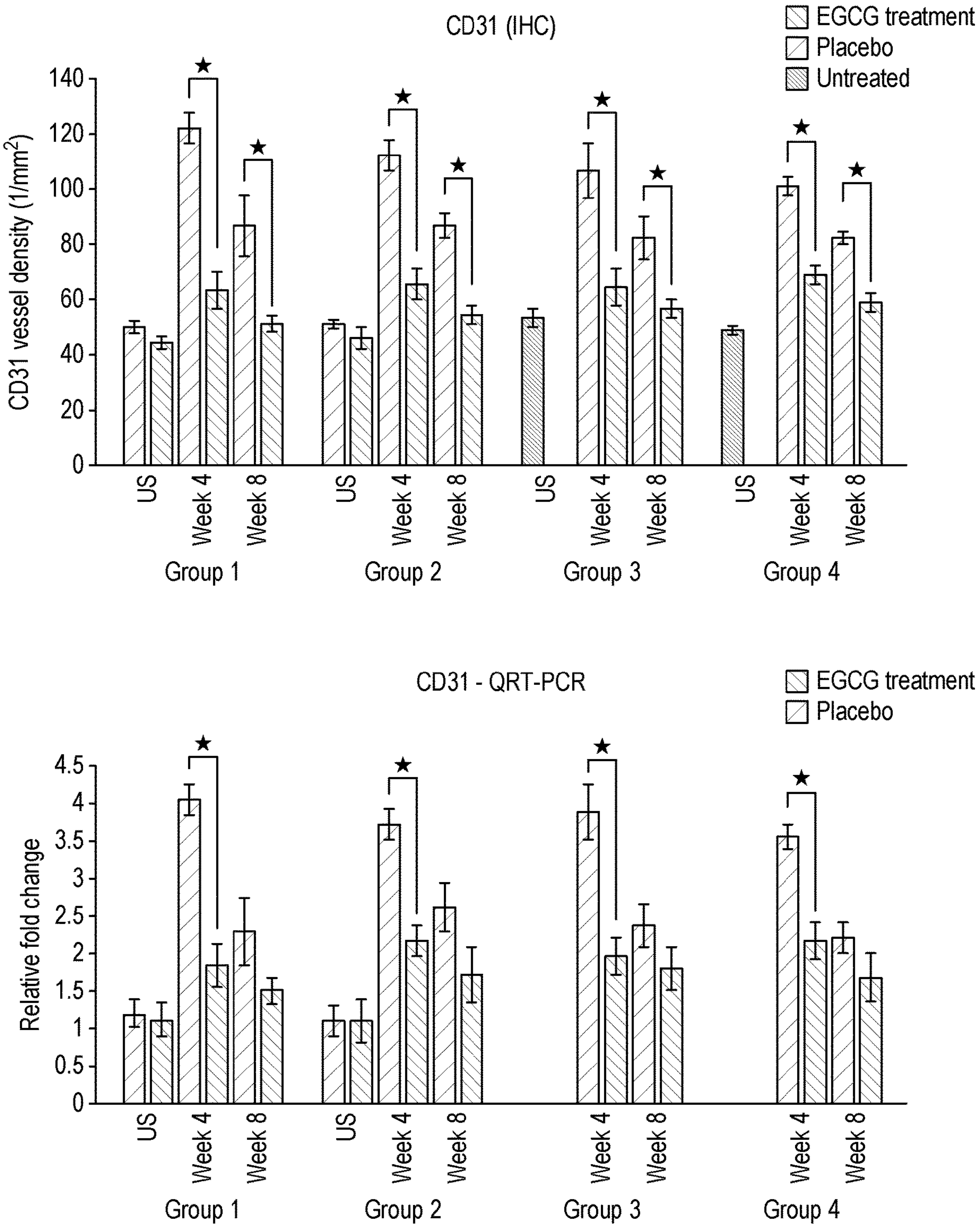

As seen from FIG. 7*a*, CD31 was significantly downregulated in EGCG-treated samples compared with placebo at weeks-4 and -8 in all groups ($p<0.01$). There was a significant difference between groups ($p=0.02$) at week-4. Group 1 was shown to have the largest reduction in CD31 compared to group-4 by 40% ($p=0.01$). QRT-PCR for CD31 demonstrated significant down regulation at week-4 in all groups in EGCG-treated samples compared to placebo samples.

Figure 7B:
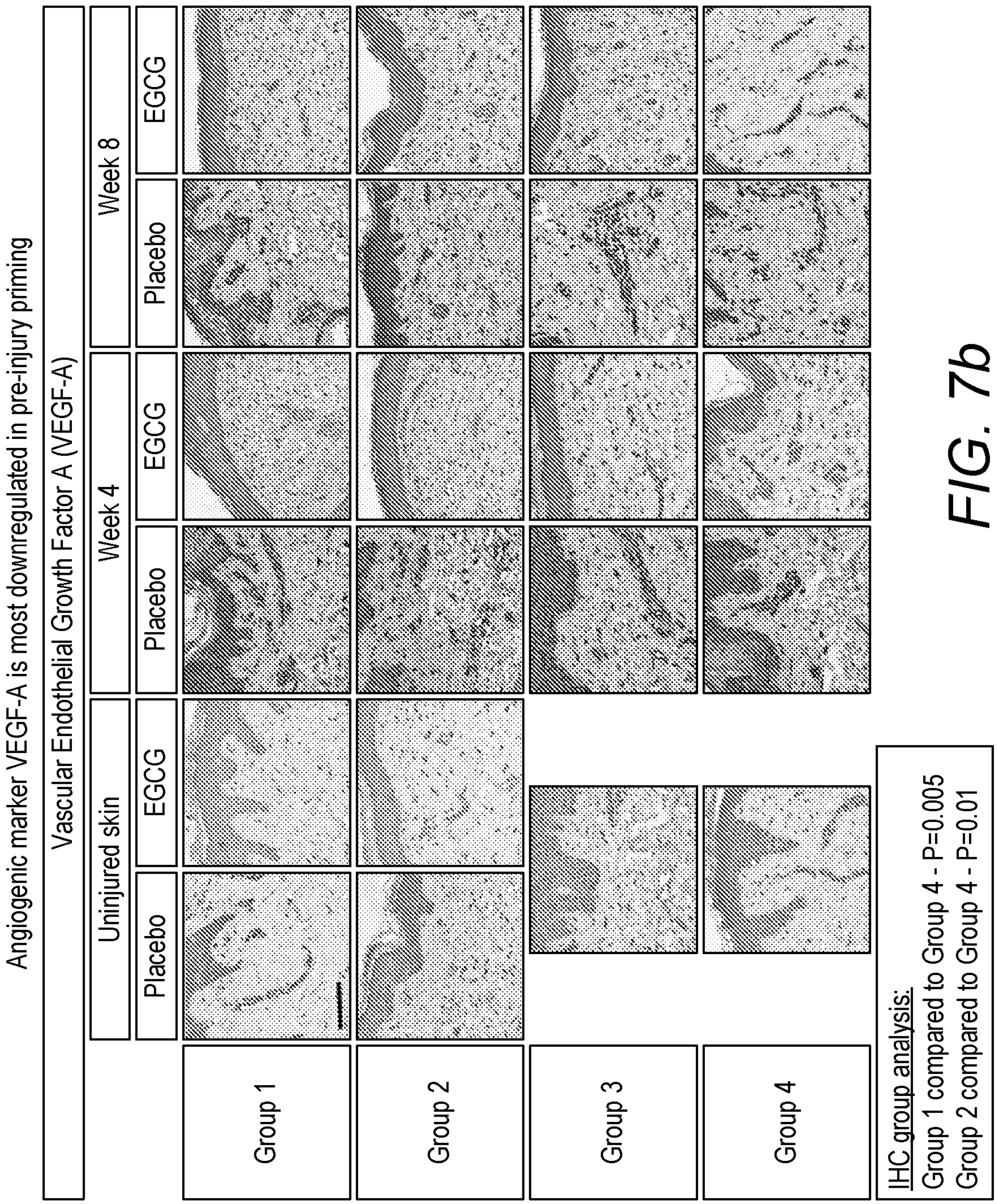

To further corroborate these findings, and is seen from FIG. 7*b*, VEGF-A was shown to be significantly downregulated at week-4 in all groups in EGCG-treated samples compared to placebo ($p<0.01$). Furthermore, groups 1-3 showed that there was a significant reduction at week-8 in EGCG-treated samples ($p<0.01$). Between group analysis demonstrated a significant difference ($p=0.003$) at week-4. This difference was found to be that group-1-2 had significantly greater reductions compared to group-4 (51%: $p=0.005$, 56%:$p=0.01$ respectively). Gene expression analysis of VEGF-A displayed significant reductions in EGCG-treated samples compared to placebo at week-4 ($p<0.05$) in groups 1-2 and 4, although there were no significant differences between groups.

Accordingly, it was observed that angiogenic markers are most downgraded in pre-injury priming.

Anti-Oxidant Effects

Oxidative stress is derived from an imbalance of oxygen and nitrogen-based free radical production, the cellular anti-oxidant defence system, and is important in fibrosis with effects on the cellular pathways of relevance to tissue repair.

Figure 8:
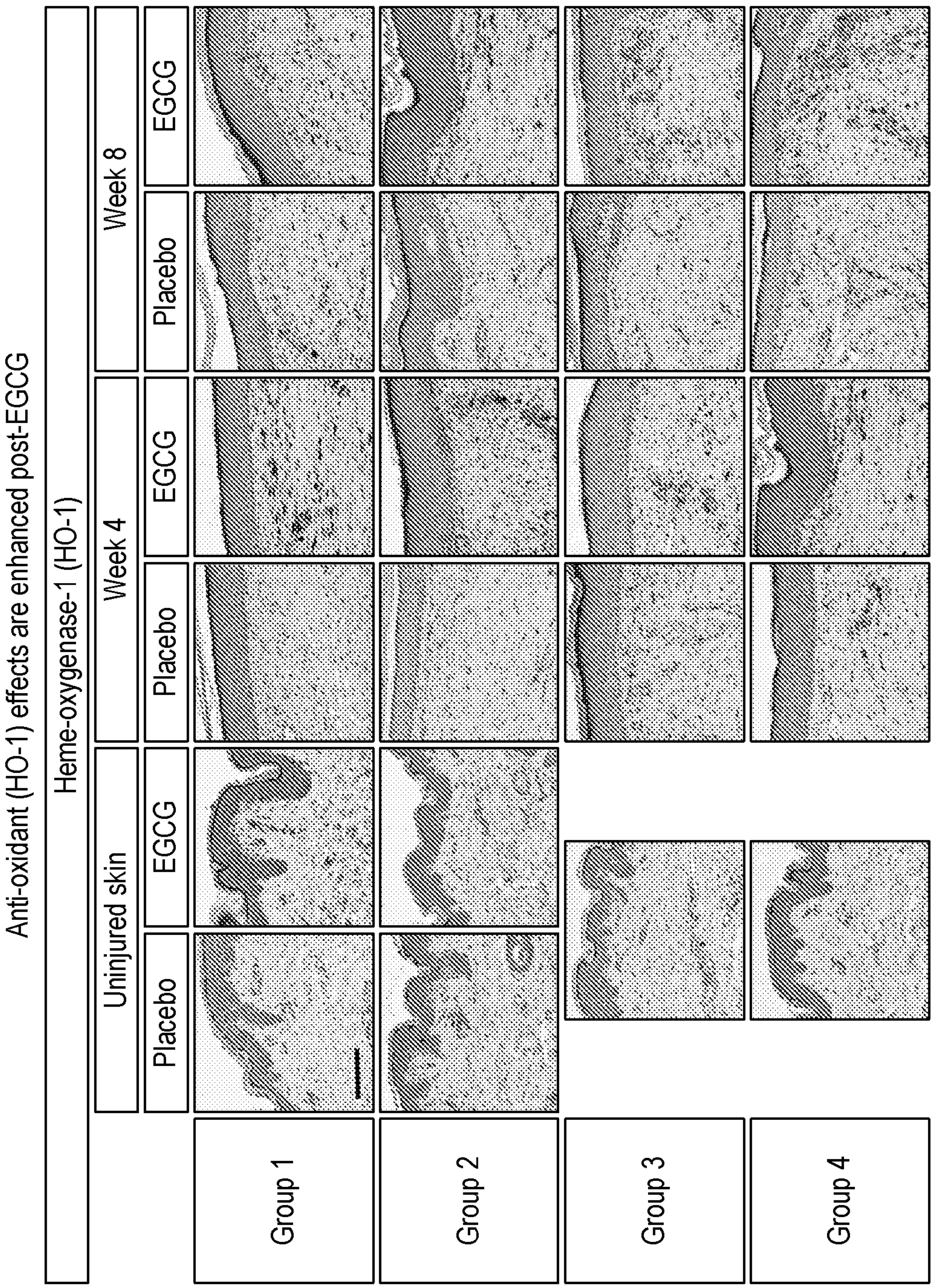
FIG. 8 shows anti-oxidant effects comparing the use of EGCG with the placebo by Heme-oxygenase 1 (HO-1) immunohistochemical stain images.
Figure 8:
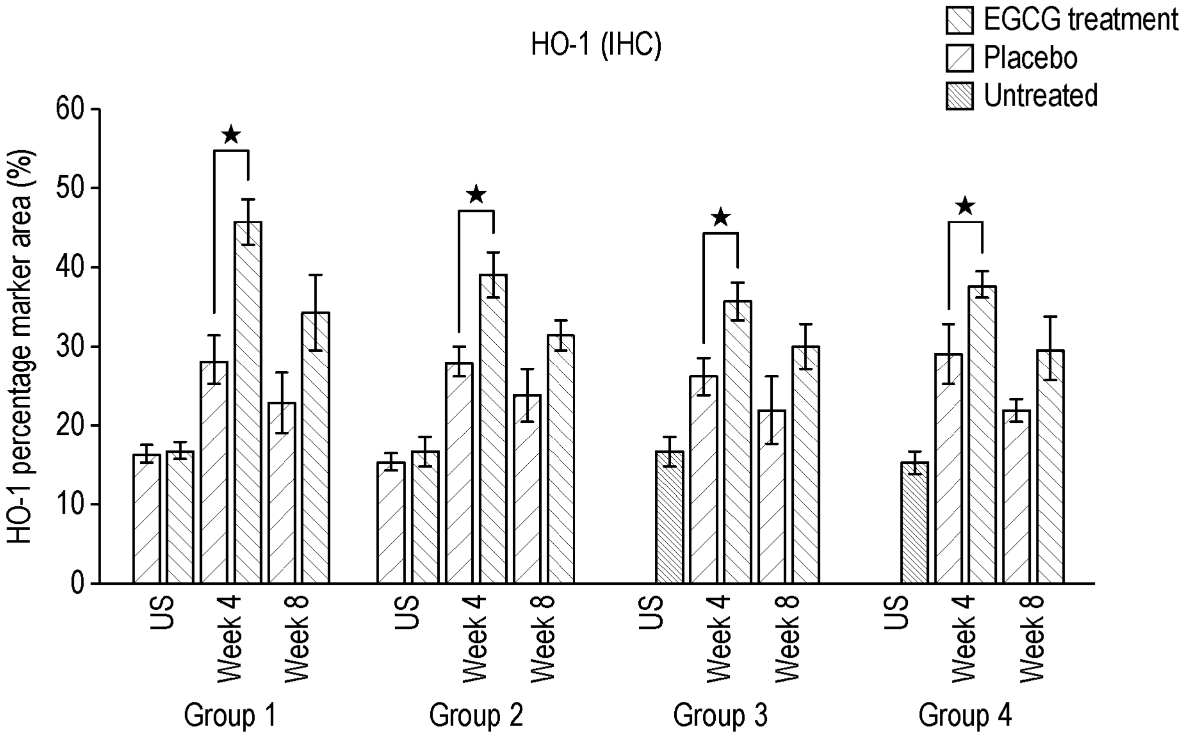

Anti-oxidants protect cells from the environment and it is known that certain topical agents, especially polyphenols, including the catechins such as EGCG, have an anti-oxidant effect. Therefore, Hemeoxygenase-1 (HO-1) and Nuclear factor erythroid 2-related factor 2 (NRF2) were used as immunohistochemical markers to identify any changes in scar samples. As shown in FIG. 8, HO-1 was found to be higher in scar tissue compared to uninjured skin at weeks-4 and 8 in all groups (scale bars=50 μm). EGCG-treated samples showed higher levels of HO-1 compared to placebo samples in all groups. This was significantly higher at week-4 in all groups ($p<0.01$), although no significant differences were found between the groups. NRF2 analysis (not shown) demonstrated the same trend where levels were greatest at week-4 and 8 compared to uninjured skin. EGCG samples had slightly higher amounts of NRF2 compared to placebo samples, although not significantly. Overall, it was observed that anti-oxidant effects are enhanced with pre-injury priming.

Scar Thickness

Figure 9:
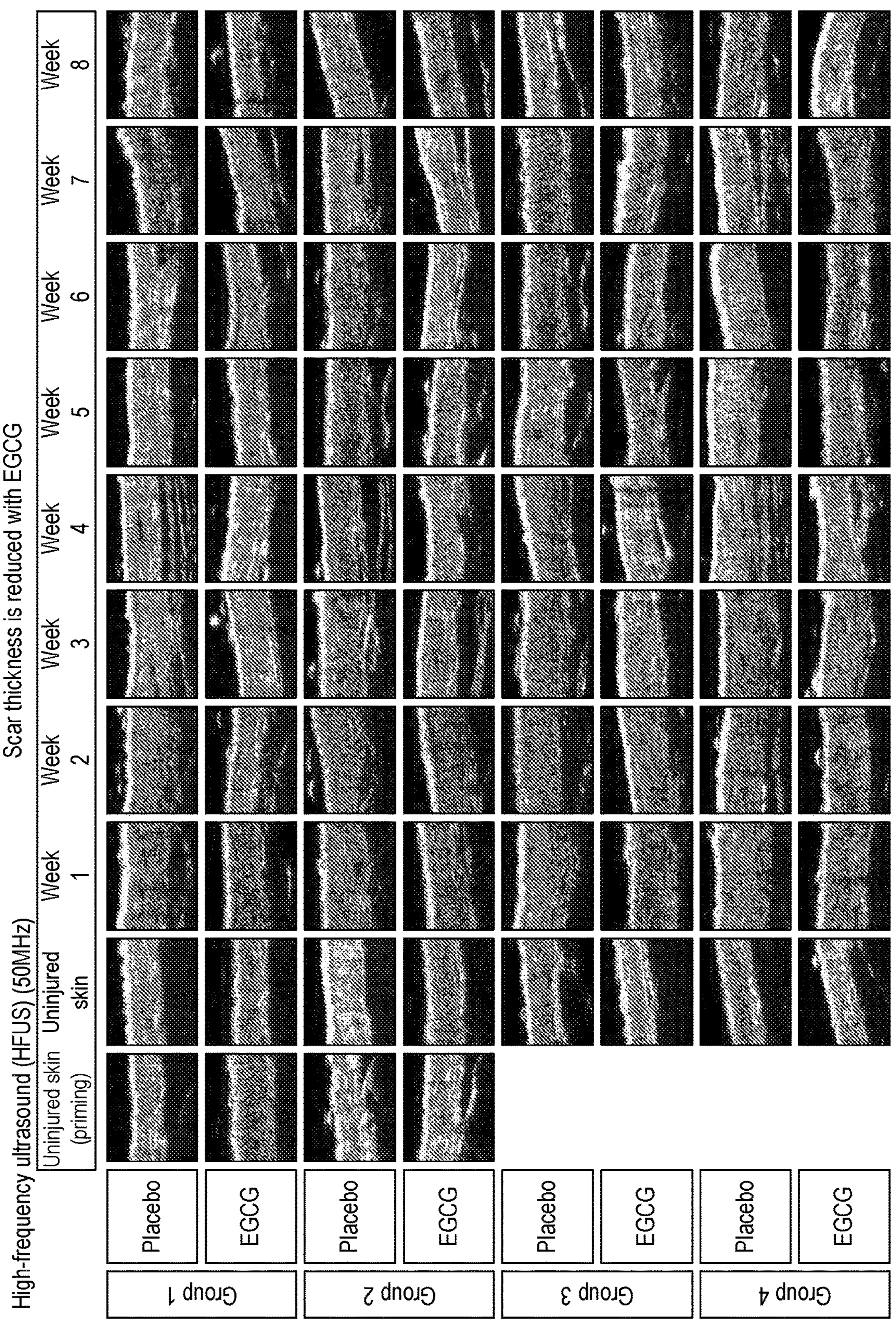
FIG. 9 shows skin structural effects comparing the use of EGCG with the placebo using high frequency ultrasound (HFUS) and H+E stain measurements.
Figure 9:
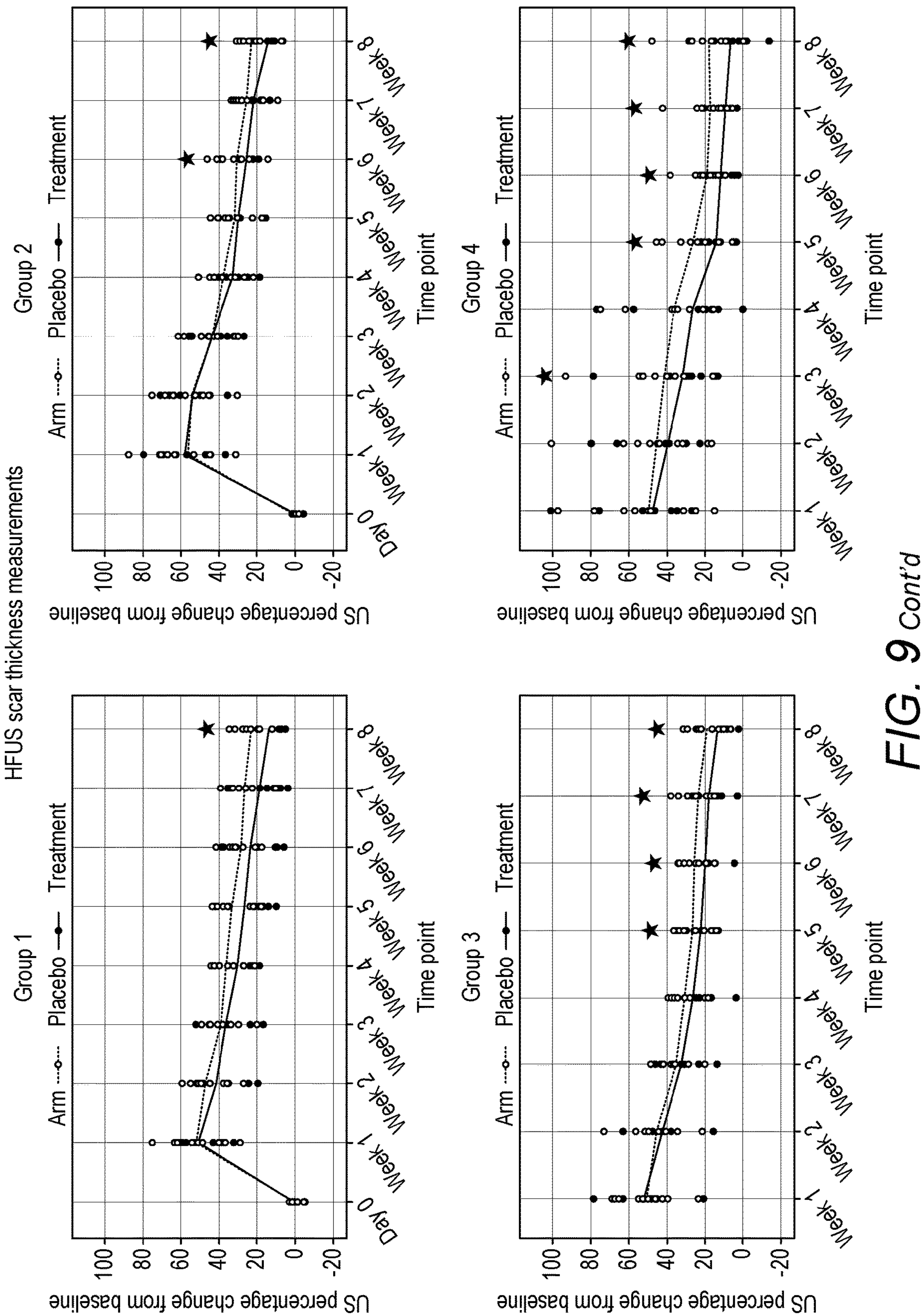
Figure 9:
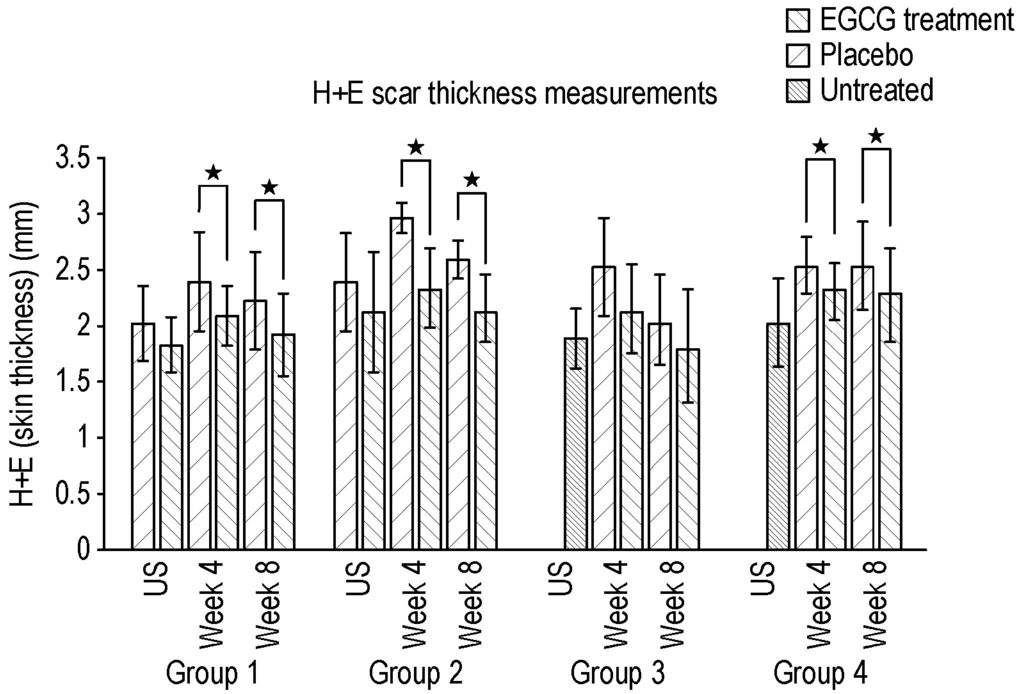

Structural changes in the scars were assessed clinically by high frequency ultrasound (HFUS) and elasticity probe, and elastin and collagen markers. HFUS was used to measure skin thickness clinically at every time point over 8 weeks. As seen from FIG. 9, skin thickness measurements were found to be lower in EGCG scars compared to placebo scars across the groups. This was significant in group-1 at week-8 ($p=0.002$), group-2 at week-6 and 8 ($p<0.01$) group-3 at weeks 5-8 ($p<0.01$) and group-4 at weeks 3, 5-8 ($p<0.01$). Scar thickness measurements using H+E stain also corroborated these findings and showed reduced scar thickness with EGCG at weeks 4 and 8 in Groups 1, 2 and 4.

Elastin Content

Figure 10:
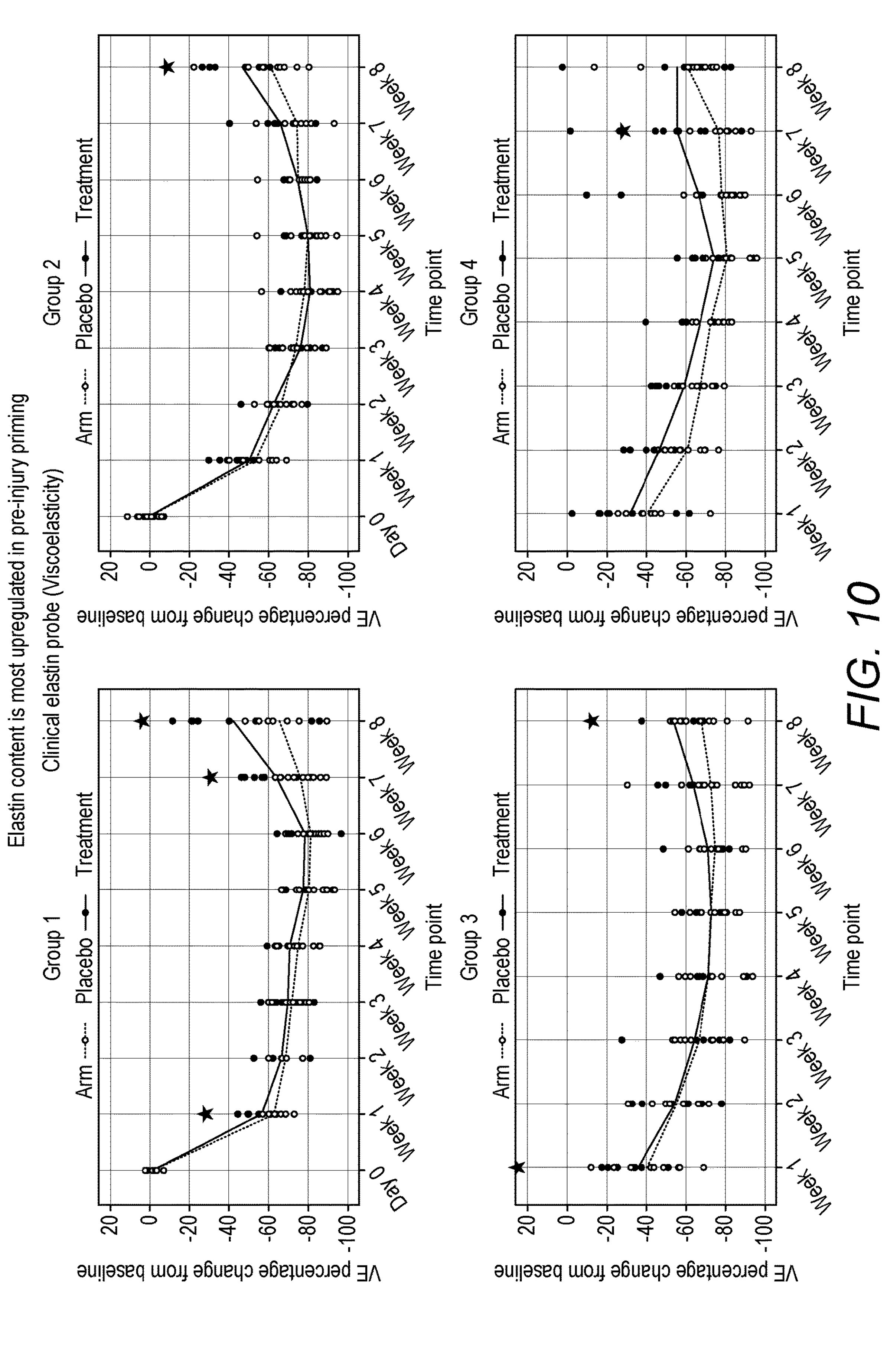
FIG. 10 shows clinical elastin probe (viscoelasticity) measurements for each of the groups comparing the use of EGCG with the placebo.
Figure 10:
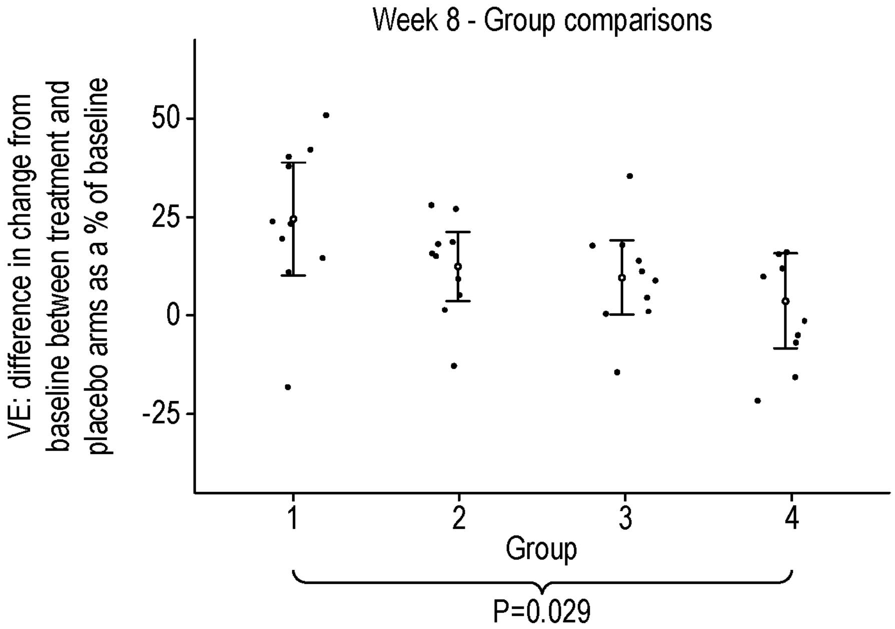

A clinical elastin probe was used to measure the viscoelasticity of the scars over 8-weeks. As shown in FIG. 10, elasticity was found to be increased in EGCG-treated arms compared to placebo-treated arms predominantly at later time points in all groups. This was significantly increased with EGCG-treated in group-1 at weeks-1, 7 and 8 ($p=0.008$, $p<0.001$, $p=0.006$ respectively), group-2 at week-8 ($p=0.005$), group-3 at week-8 ($p=0.003$) and group-4 at week-7 ($p=0.012$). Between group comparisons showed that group-1 significantly increased elastin more than group-4 at week-8 ($p=0.029$).

Figure 11:
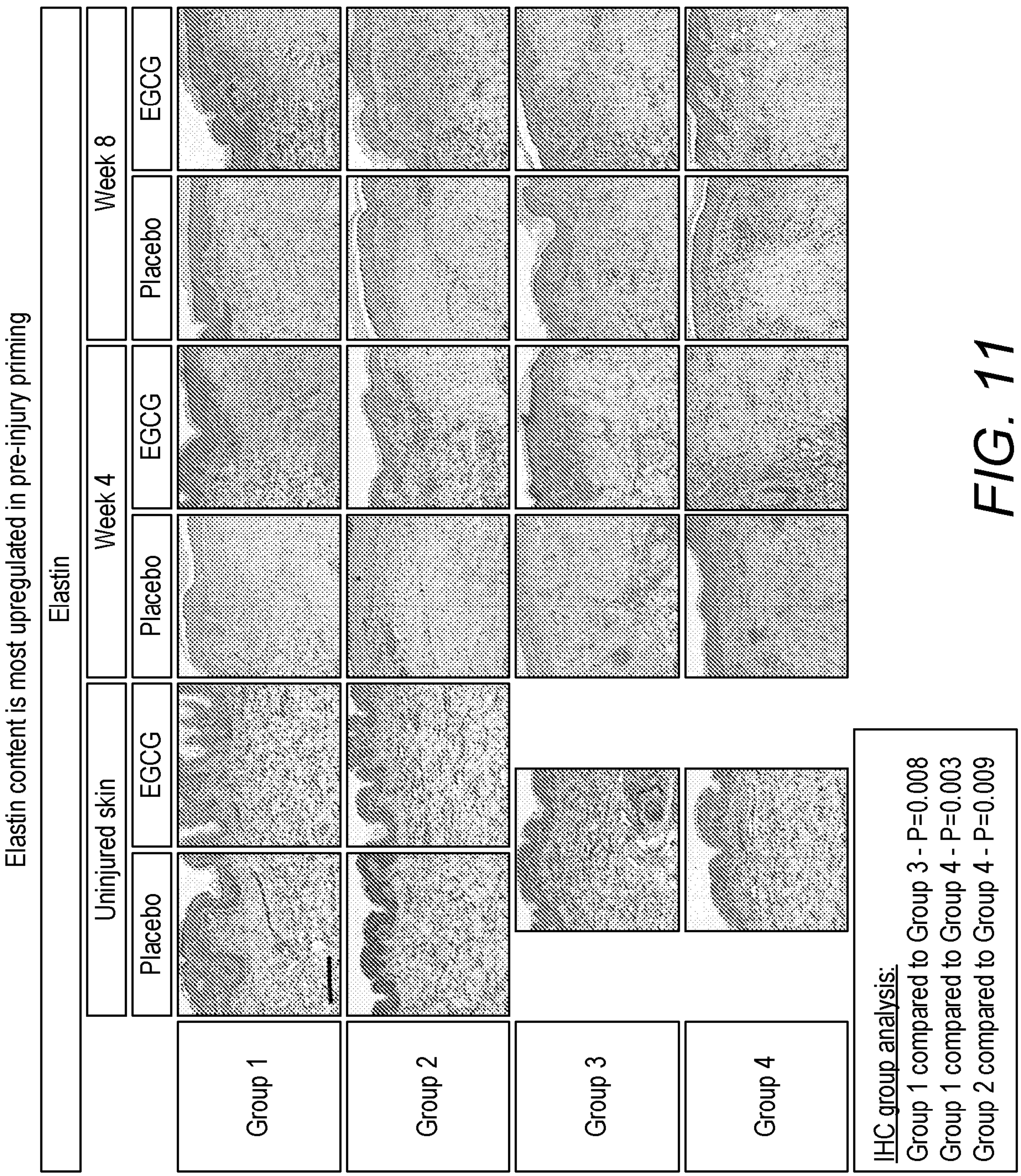
FIG. 11 shows immunohistochemical images for elastin comparing the use of EGCG with the placebo, including quantitative real-time reverse transcriptase-PCR (QRT-PCR) analysis.

As seen from FIG. 11, immunohistochemical analysis of elastin was up-regulated at week-8 in EGCG-treated samples compared to placebo samples in all groups ($p<0.01$). There was also a significant increase at week-4 in group-1 only by 12% with EGCG ($P=0.01$). Between group analysis indicated a significant difference at week-8 ($p=0.001$). The greatest differences were in group-1 compared to groups-3 by 20% ($p=0.008$) and group-4 by 20% ($p=0.003$) and in group-2 compared to group-4 by 17% ($p=0.009$). Gene expression analysis of elastin demonstrated that there was an upregulation in EGCG-treated samples compared to placebo samples at week-4 and 8, and this was significant in groups-1 to 3 at week-8 ($p<0.05$).

Thus, it was observed that elastin content is most upregulated with pre-injury priming.

Conclusions from the Trial

The double-blind, randomized placebo-controlled clinical trial quantitatively investigated the effects of different timings of application of an exemplary topical scar reducing agent (EGCG being the particular agent used in the trial) versus a placebo in relation to inflammatory response, angiogenesis, anti-oxidant effects and structural changes in cutaneous skin scarring in healthy human volunteers.

The findings demonstrated that EGCG topical application: 1) Mast cell (MCT, MCC and CKit) number was significantly reduced; 2) Blood flow and angiogenesis (CD31 and VEGF-A expression) were significantly reduced; 3) Anti-oxidant effect was enhanced by increased HO-1 levels; 4) Scar thickness was reduced; 5) Viscoelasticity increased and elastin expression was significantly increased.

The unique concept of priming the skin with a topical agent, such as EGCG, prior to wounding in human skin scarring had, to the Applicant's knowledge, not been contemplated prior to this study. Contrary to conventional methods of delayed topical application following scar formation, and the inventor's more recent method of zonal priming on the day of injury, the present study unexpectedly demonstrated that the pre-emptive pre-injury priming groups (by 7-days (group-1) or 3-days (group-2)) gave rise to superior results in comparison to immediate (group-3) or delayed topical application groups (group-4).

Based on immunohistochemical data, and as summarised in the table in FIG. 12, mast cell analysis by MCT, MCC and CKit demonstrated that at week-4, Group-1 showed greater reductions than group-3 (53%, 29%, 26% respectively) and group-4 (52%, 41%, 27% respectively), whilst group-2 showed greater reductions in MCC compared to group-4 (29%). Angiogenesis analysis by CD31 and VEGF-A showed that group-1 was optimal compared to group-4 (40%, 51% respectively) at week-4 and group-2 reduced VEGF-A levels more than group-4 (56%). Elastin content was significantly increased in groups-1 and 2 compared to group-4 (20%, 17% respectively) at week-8 and this was supported by clinical elastin measurements in group-1 at week-8. There were also differences noted in the primed uninjured skin prior to injury indicating that pre-emptively applying EGCG reduces the resident mast cell population, reduces angiogenic markers and increases elastin levels initially prior to the effects becoming more pronounced when the injury occurs and with further topical application.

The aforementioned study has demonstrated that pre-emptive pre-injury priming of skin with a topical agent, such as EGCG, has significant beneficial effects on human cutaneous skin scarring by reducing mast cells, angiogenesis, skin thickness and simultaneously increasing elastin content. While the study itself was confined to use of EGCG, it is expected that pre-emptive priming with other polyphenols, which are similarly known for their anti-oxidant effects, will also lead to improvements in cutaneous scarring as compared to when their use is commenced immediately following surgery or when delayed.

Figure 13:
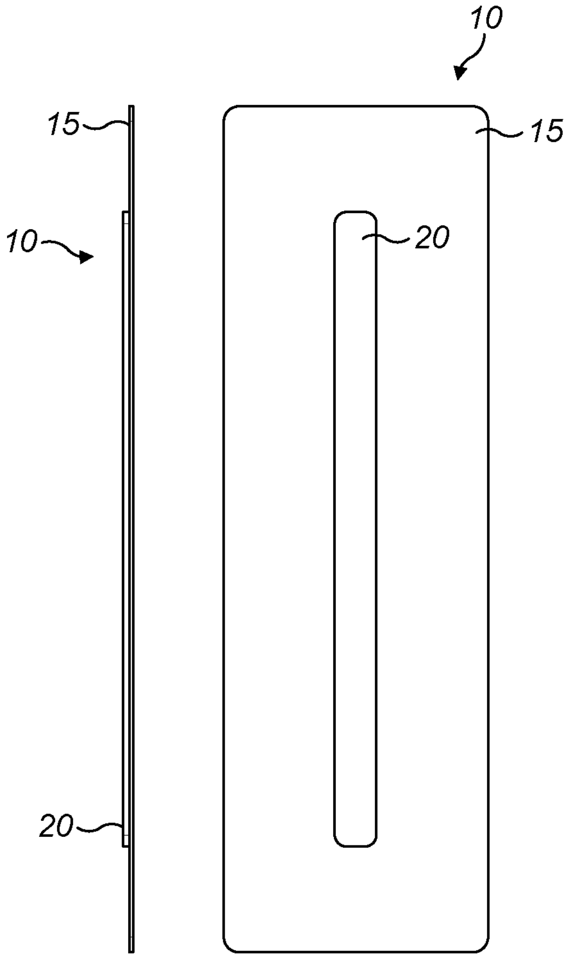
FIG. 13 shows a surgical dressing in accordance with an embodiment of the invention.

FIG. 13 shows a dermal skin patch (10) in accordance with one aspect of the invention. The patch (10) comprises an adhesive silicone sheet (15) and a gel strip (20) which is impregnated with a dose of EGCG. When used pre-surgery, the patch is applied so that the EGCG-containing gel strip is in contact with the skin at the site where the surgical incision or laser therapy is planned. The patch is intended to be replaced every 12-24 hours and several such patches may be applied over a 3 to 7-day period leading up to the surgery. The patches may continue to be used post-surgery until scar erythema (wound inflammation) has completely subsided, as an alternative to direct application of a topical scar-improving agent in a liquid or semi-solid formulation.

The dermal skin patch (10) is not limited to the relative dimensions shown in the drawing, and other shapes and sizes may be selected according to the planned surgical procedure and likely size of the resulting wound. For example, for a puncture-type wound, such as in the case of a biopsy, the patch may comprise a circular silicone sheet and the impregnated gel applied in a concentric circle within the boundary of the sheet so that there is sufficient adhesive contact between the silicone and the skin around the impregnated gel to hold the patch in position.

Although particular aspects and embodiments of the invention have been disclosed herein in detail, this has been done by way of example and for the purpose of illustration only. The aforementioned aspects and embodiments are not intended to be limiting with respect to the scope of the appended claims, which follow. It is contemplated that various substitutions, alterations and modifications may be made to the invention without departing from the scope of the invention defined by the claims.

The invention claimed is:

1. A method for preemptively priming a skin surface at a surgical site, the method comprising topically administering to the surgical site, prior to surgery, a composition comprising a catechin, wherein the catechin is (-)-epigallocatechin-3-gallate, and wherein the administering is commenced at least 3 days prior to the surgery.

2. The method according to claim 1, wherein the administering commences from 3 to 7 days prior to surgery.

3. The method according to claim 1, wherein the catechin is present in the composition in an amount of from about 1 to 15 mol %.

4. The method according to claim 1, wherein the composition further comprises a topical carrier.

5. The method according to claim 4, wherein the composition is in a form selected from the group consisting of a cream, a paste, a lotion, a gel, a liquid, a foam, a solution, a suspension, a balm, a spray, a wax, a paste, and an ointment.

6. The method according to claim 1, wherein the composition is impregnated in a surgical dressing.

7. The method according to claim 6, wherein the surgical dressing is a dermal patch comprising a silicone layer, wherein the catechin is impregnated in the silicone layer or in an additional layer, wherein the surgical dressing is configured so that the layer impregnated with the catechin is placed over the skin surface at the surgical site prior to surgery.

8. A method for minimizing a surgical scar on a skin surface of a subject, the method comprising topically administering to a surgical site, prior to surgery, a composition comprising a catechin, wherein the catechin is (-)-epigallocatechin-3-gallate, and wherein the administering is commenced at least 3 days prior to the surgery.

9. The method according to claim 8, wherein the administering commences from 3 to 7 days prior to surgery.

10. The method according to claim 8, wherein the administering is continued until about 1 to 10 weeks post-surgery.

11. The method according to claim 8, wherein the composition is administered to the surgical site at least once daily.

12. The method according to claim 8, wherein the administering reduces the risk of raised dermal scarring on the skin surface at the surgical site, wherein raised dermal scarring comprises hypertrophic scarring and/or keloid scarring.

13. A method for increasing elastin content in skin at a surgical site, the method comprising topically administering to the surgical site, prior to surgery, a composition comprising a catechin, wherein the catechin is (-)-epigallocatechin-3-gallate, and wherein the administering is commenced at least 3 days prior to the surgery.

14. The method according to claim 13, wherein the administering commences from 3 to 7 days prior to surgery.

15. The method according to claim 13, wherein the administering reduces the risk of raised dermal scarring on the skin surface at the surgical site, wherein raised dermal scarring comprises hypertrophic scarring and/or keloid scarring.

* * * * *